US012239808B2

(12) United States Patent
Tandon et al.

(10) Patent No.: US 12,239,808 B2
(45) Date of Patent: Mar. 4, 2025

(54) HAND TOOL FOR AIDING IN INSERTION OF A TRANS-ROUND WINDOW MEMBRANE CATHETER FOR MICROPUMP-MEDIATED ACUTE AND CHRONIC INNER-EAR DRUG DELIVERY

(71) Applicant: Charles Stark Draper Laboratory, Inc., Cambridge, MA (US)

(72) Inventors: Vishal Tandon, Somerville, MA (US); Ernest Kim, Cambridge, MA (US); Jeffrey Borenstein, West Roxbury, MA (US)

(73) Assignee: Charles Stark Draper Laboratory, Inc., Cambridge, MA (US)

( * ) Notice: Subject to any disclaimer, the term of this patent is extended or adjusted under 35 U.S.C. 154(b) by 239 days.

(21) Appl. No.: 17/100,335

(22) Filed: Nov. 20, 2020

(65) Prior Publication Data
US 2021/0154452 A1    May 27, 2021

Related U.S. Application Data

(60) Provisional application No. 62/938,561, filed on Nov. 21, 2019.

(51) Int. Cl.
*A61M 31/00*       (2006.01)

(52) U.S. Cl.
CPC ....... *A61M 31/002* (2013.01); *A61M 2205/02* (2013.01); *A61M 2205/04* (2013.01);
(Continued)

(58) Field of Classification Search
CPC ... A61F 11/006; A61F 11/20; A61M 5/14276; A61M 5/1428; A61M 25/065;
(Continued)

(56) References Cited

U.S. PATENT DOCUMENTS

| | | | | |
|---|---|---|---|---|
| 5,895,372 A | * | 4/1999 | Zenner | A61M 5/1428 604/93.01 |
| 5,990,380 A | * | 11/1999 | Marotta | A61L 29/106 427/2.28 |

(Continued)

FOREIGN PATENT DOCUMENTS

| | | |
|---|---|---|
| CN | 104703650 A | 6/2015 |
| CN | 105555355 A | 5/2016 |

(Continued)

OTHER PUBLICATIONS

International Preliminary Report on Patentability on PCT Appl. Ser. No. PCT/US2020/061565 dated Jun. 2, 2022 (9 pages).
(Continued)

*Primary Examiner* — Kami A Bosworth
(74) *Attorney, Agent, or Firm* — Foley & Lardner LLP

(57) ABSTRACT

The present solution provides systems and methods for trans-round window membrane drug delivery. As an overview, a system can include a micropump that is connected to a flexible cannula. The cannula can be threaded through a handpiece that can be used to pierce the round window membrane of a patient. Using the handpiece, the cannula can be inserted through the round window membrane to improve the distribution of the delivered drug throughout the inner ear. The present solution can function as a small implantable or wearable device that can be used for both chronic and acute trans-round window membrane drug delivery. With this configuration, the micropump can constantly or intermittently deliver, over a period of days to months, small volumes of drugs from an internal reservoir.

11 Claims, 15 Drawing Sheets

(52) U.S. Cl.
CPC .............. *A61M 2205/3337* (2013.01); *A61M 2205/583* (2013.01); *A61M 2210/0662* (2013.01)

(58) Field of Classification Search
CPC ...... A61M 25/0662; A61M 2025/0004; A61M 2025/0006; A61M 2025/0656; A61M 2025/0681; A61M 31/00; A61M 31/002; A61M 2205/04; A61M 2210/0662; A61M 25/0045; A61M 2039/068; A61M 2205/0238; A61L 29/08–106
See application file for complete search history.

(56) References Cited

U.S. PATENT DOCUMENTS

| | | | | |
|---|---|---|---|---|
| 6,377,849 | B1 * | 4/2002 | Lenarz | A61M 25/04 604/21 |
| 2004/0069717 | A1 | 4/2004 | Laurell et al. | |
| 2006/0264897 | A1 | 11/2006 | Lobl et al. | |
| 2008/0009836 | A1 * | 1/2008 | Fiering | A61M 5/14276 604/891.1 |
| 2015/0032124 | A1 | 1/2015 | Lenarz et al. | |
| 2017/0367892 | A1 | 12/2017 | Kim et al. | |
| 2019/0117884 | A1 | 4/2019 | Peppi et al. | |

FOREIGN PATENT DOCUMENTS

| | | |
|---|---|---|
| EP | 1 004 326 A2 | 5/2000 |
| JP | 2008-537684 A | 9/2008 |
| JP | 2019-522539 A | 8/2019 |

OTHER PUBLICATIONS

International Search Report and Written Opinion on PCT Appl. Ser. No. PCT/US2020/061565 dated Feb. 17, 2021 (14 pages).
Office Action issued in corresponding Chinese Patent Application No. 202080093880.5 dated Mar. 22, 2024 (15 pages).
Office Action issued in corresponding Japanese Patent Application No. 2022-529969 dated Oct. 29, 2024 (9 pages).

* cited by examiner

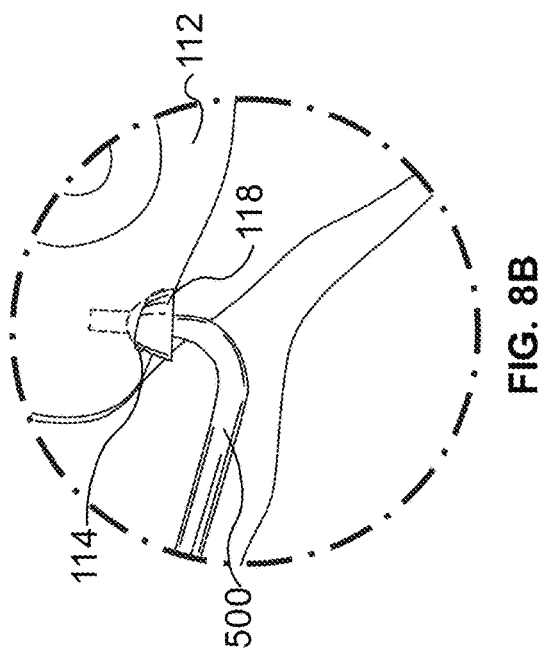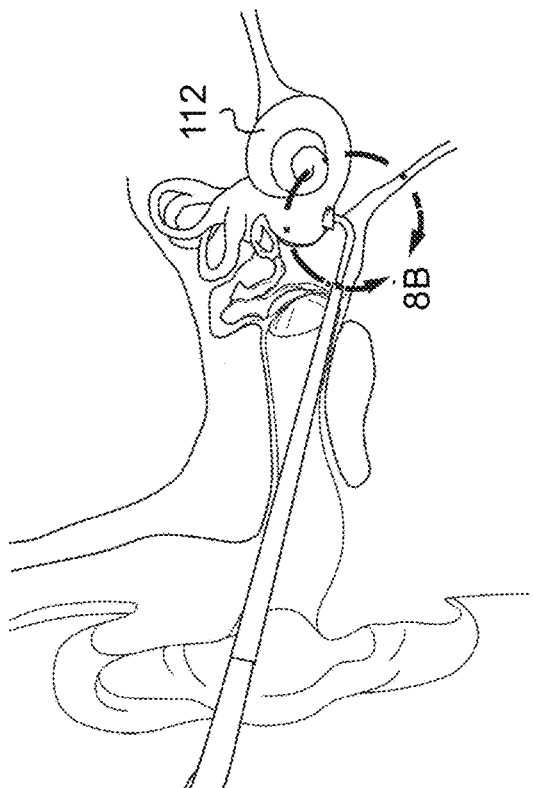

HAND TOOL FOR AIDING IN INSERTION OF A TRANS-ROUND WINDOW MEMBRANE CATHETER FOR MICROPUMP-MEDIATED ACUTE AND CHRONIC INNER-EAR DRUG DELIVERY

CROSS REFERENCE TO RELATED APPLICATIONS

The present application claims priority under 35 U.S.C. § 119(e) to U.S. Provisional Patent Application No. 62/938,561, titled "HAND TOOL FOR AIDING IN INSERTION OF A TRANS-ROUND WINDOW MEMBRANE CATHETER FOR MICROPUMP-MEDIATED ACUTE AND CHRONIC INNER-EAR DRUG DELIVERY," filed Nov. 21, 2019, which is incorporated herein in its entirety by reference.

BACKGROUND

Advances in pharmacological technology have provided a number of compounds for the treatment of sudden noise and age-related hearing loss. While these new compounds show promising results, many of them have failed to be effective when delivered systemically due to the blood-cochlear barrier, and local delivery by deposition onto the round window membrane of the patient is often ineffective because penetration of the compounds through the round window membrane can be low. The low penetration of the compounds can result in the delivery of compound concentration levels below the therapeutic threshold.

SUMMARY

The present disclosure describes systems and methods that can provide a robust procedure for the effective, local delivery of medications (or more generally, compounds) to the inner ear. The systems and methods can deliver the compounds to the inner ear via a trans-round window membrane (trans-round window membrane) approach using a cannula (also referred to herein as a catheter) inserted through the round window membrane and connected to an implanted micropump. The micropump can deliver compounds acutely or chronically. The micropump can control the amount of compound delivered directly into the perilymphatic fluid of the scala tympani. The systems and methods can overcome many difficulties that arise from intra-tympanic injections, such as low quantity of drugs crossing the round window membrane, uneven distribution of drug across the inner ear, and poor drug bioavailability within the cochlea. The systems and methods can be applied both to pharmacokinetics studies, in vivo drug discovery, and the treatment of inner ear diseases in humans. Trans-round window membrane drug delivery is compatible with numerous drug types, including small molecule and large complex molecules such as proteins, viruses, and liposomes.

The systems and methods of this disclosure can also be used to overcome challenges involved in implanting the cannula into the patient for chronic treatment. For example, this disclosure provides a tool, referred to herein as a handpiece, which can be used to facilitate insertion of the cannula through the round window membrane, or other anatomic membrane in an ear, of a patient. The cannula can be threaded through a channel included in the handpiece and the handpiece can be used to pierce the round window membrane. The handpiece can then be pulled away from the middle ear, while the cannula remains behind due to friction between the cannula and the round window membrane. The cannula may also include a bleb or stopper to facilitate seating the cannula within the round window membrane, as well as controlling a depth to which the cannula protrudes into the inner ear.

At least one aspect of the present disclosure is directed to method to deliver a fluid to an inner ear. The method can include introducing a cannula into a channel defined by a tool shaft of a handpiece. The handpiece can include a tip portion coupled with the tool shaft and comprising an outlet in communication with the channel. The handpiece can include a collar coupled with the tip portion a predetermined distance from the outlet. The collar can be configured to seat with an anatomic structure of the patient and control a distance the tip portion projects into a cochlea of the patient. The method can include piercing an anatomic membrane covering the anatomic structure of a patient with the tip portion of the handpiece. The method can include implanting the cannula into the patient via the outlet of the handpiece. The cannula can include a first end coupled with a micropump and a second end comprising a stopper. The stopper can be configured to enable a cannula tip to be inserted through the anatomic membrane and into a cochlea of a patient. The method can include seating the stopper of the cannula into the anatomic structure of the patient. The method can include withdrawing the handpiece from an ear of the patient.

In some implementations, the method can include implanting the micropump in the patient. The micropump comprises a drug reservoir storing a compound. In some implementations, the method can include pumping, by the micropump, the compound from the drug reservoir to the cochlea of the patient via the cannula. In some implementations, the method can include withdrawing, by the micropump, a predetermined volume of a fluid from the cochlea of the patient responsive to pumping the compound from the drug reservoir to the cochlea via the cannula. In some implementations, the micropump can include a first valve, a second valve, a pump, a loading chamber, and an outlet fluidly connected to the cannula.

In some implementations, the method can include drawing the compound from the drug reservoir into the loading chamber by opening the first valve and activating the pump. In some implementations, the method can include forcing the compound through the outlet to the cannula by closing the first valve, opening the second valve, and activating the pump. In some implementations, the method can include securing, prior to withdrawing the handpiece from the ear of the patient, the cannula in place using at least one of the stopper or a glue. In some implementations, the method can include providing an additional volume of the compound to the drug reservoir via an external reservoir. In some implementations, the method can include selecting a length of the tip portion of the handpiece based on a computed tomography scan or a magnetic resonance imaging scan of the patient.

At least one other aspect of the present disclosure is directed to a system. The system can include a cannula. The cannula can have a first end coupled with a micropump. The cannula can have a second end comprising a stopper. The stopper can be configured to enable a cannula tip to be inserted through an anatomic membrane and into a cochlea of a patient. The system can include a handpiece configured to introduce the cannula to the patient. The handpiece can include a channel defined by a tool shaft of the handpiece. The channel can be configured to receive the cannula. The handpiece can include a tip portion coupled with the tool shaft and comprising an outlet in communication with the channel. The tip portion can be configured to pierce the anatomic membrane of the patient. The handpiece can include a collar coupled with the tip portion a predetermined distance from the outlet. The collar can be configured to seat with an anatomic structure of the patient and control a distance that the tip portion can project into the cochlea of the patient. The handpiece can be configured to be withdrawn from an ear of the patient responsive to seating the cannula into the anatomic structure of the patient.

In some implementations, the micropump can be implanted in the patient. In some implementations, the micropump can include a drug reservoir storing a compound. In some implementations, the micropump can pump a compound from the drug reservoir to the cochlea of the patient via the cannula. In some implementations, the micropump can withdraw a predetermined volume of a fluid from the cochlea of the patient after pumping the compound from the drug reservoir to the cochlea via the cannula. In some implementations, the micropump can include a first valve, a second valve, a pump, a loading chamber, and an outlet fluidly connected to the cannula. In some implementations, the micropump can draw the compound from the drug reservoir into the loading chamber by opening the first valve and activating the pump. In some implementations, the micropump can force the compound through the outlet to the cannula by closing the first valve, opening the second valve, and activating the pump.

In some implementations, the handpiece can include an angled portion coupling the tip portion to the tool shaft. The angled portion can have a second channel in communication with the channel and the outlet of the tip portion. In some implementations, at least one of the angled portion or the tip portion are separable from the tool shaft, and can be coupled together using one or more of a snap-on connector, a friction fit connection, a press-fit connection, a knurled nut, or a Luer lock connection. In some implementations, the angled portion, the tip portion, and the tool shaft are manufactured from a single contiguous piece of material comprising at least one of stainless steel or a plastic. In some implementations, at least one of the angled portion or the tip portion can rotate, while coupled to the tool shaft, around an axis parallel to a length of the tool shaft.

In some implementations, the tip portion of the handpiece includes a needle tip portion. In some implementations, the needle tip portion can pierce the anatomic membrane of the patient. In some implementations, the outlet of the tip portion is positioned at a distal end of the tip portion. In some implementations, the distal end of the tip portion forming an angle between the outlet and the tip portion, wherein the angle is between 70 degrees and 170 degrees, between 75 degrees and 130 degrees, between 90 degrees and 120 degrees, or between 110 degrees and 120 degrees. In some implementations, a length of the tool shaft is between about 130 mm and about 170 mm, between about 140 mm and about 160 mm, or between about 140 mm and about 150 mm.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification. Aspects can be combined and it will be readily appreciated that features described in the context of one aspect of the invention can be combined with other aspects. Aspects can be implemented in any convenient form.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. The foregoing and other objects, aspects, features, and advantages of the disclosure will become more apparent and better understood by referring to the following description taken in conjunction with the accompanying drawings, in which:

FIGS. 8A and 8B illustrates the tip of the example handpiece inserted into a round window, in accordance with one or more implementations;

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The present solution provides trans-round window membrane drug delivery. As an overview, the system can include a micropump that is connected to a flexible cannula. The cannula can be inserted through the round window membrane using a handpiece tool. The present solution can function as small implantable or wearable device that can be used for both chronic and acute trans-round window membrane drug delivery. With this configuration, the micropump can constantly or intermittently deliver, over a period of days to months, small volumes of drugs from an internal reservoir. In some implementations, syringe pumps can be used for acute procedures. The micropump can drive fluid flow through a cannula to deliver multiple doses on a pre-programmed schedule. The solution is compatible with delivery of a timed series of several agents.

The present solution can be used in place of (or in conjunction with) systemic drug delivery. Systemic delivery can require higher doses of compounds when compared to the local compound delivery provided by the present solution. The high doses associated with systemic delivery can often produce undesirable side effects that, in some cases, discourage patients from continuing treatment. Moreover, systemically administered drugs often are modified by hepatocytic enzymes once drugs pass the hepatic system, further reducing drug activity and producing a poor therapeutic effect in the inner-ear. By delivering the compounds directly to the inner ear, the present solution can overcome these problems with systemic drug delivery because the compounds are injected directly into cochlear fluids. Direct injection of the compounds into the cochlear fluids enables a smaller dose when compared to systemic delivery.

This disclosure also provides a tool, referred to herein as a handpiece, which can be used to facilitate insertion of the cannula through an anatomic membrane, such as the round window membrane, of a patient. The handpiece can be operated, for example, by a surgeon. The cannula can be threaded through a channel included in the handpiece and the handpiece can be used to pierce the round window membrane. The handpiece can then be pulled away from the middle ear, while the cannula remains behind due to friction between the cannula and the round window membrane. The cannula may also include a bleb or stopper to facilitate seating the cannula within the round window membrane, as well as controlling a depth to which the cannula protrudes into the inner ear. The handpiece and the cannula, as well as techniques for using both, are described further below.

Figure 1:
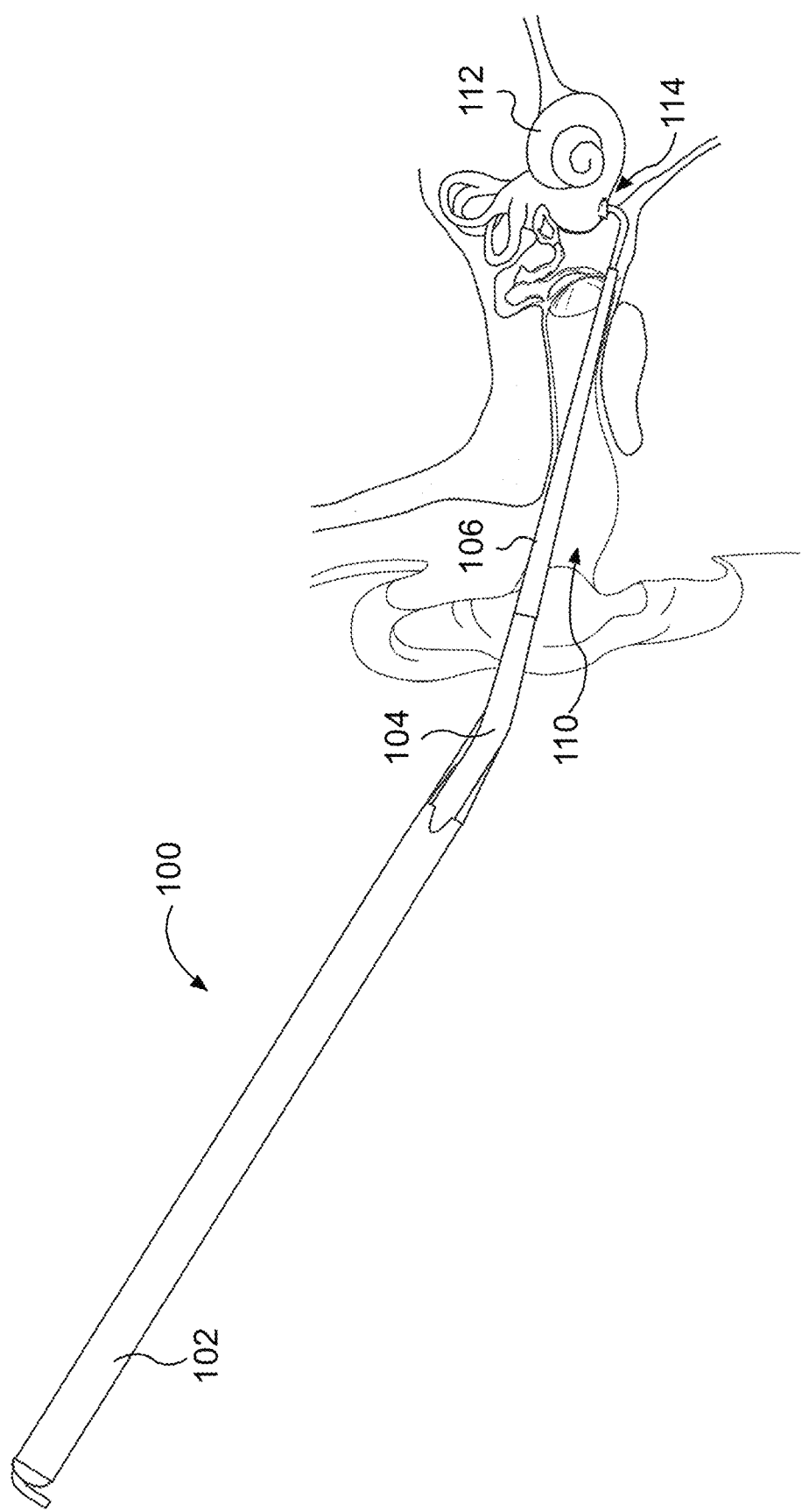
FIG. 1 illustrates an example handpiece delivering fluid to the inner ear of a patient, in accordance with one or more implementations.

FIG. 1 illustrates an example handpiece 100 delivering fluid to the inner ear of a patient. The fluid can be any therapeutic substance or therapeutic agent. The handpiece 100 includes a tool shaft 102, an angled portion 104, and a tip portion 106. The tip portion 106 can also include a collar 108. The handpiece 100 is inserted into the ear canal 110 of the patient for the transcanal delivery of fluid to the cochlea 112 via the round window 114. The tip portion 106 can be used to pierce the round window membrane to enable fluid to be delivered to the cochlea 112.

The tool shaft 102 can be held in the hand of a surgeon or robotic surgical device, and can define a cavity, or channel, through its center. The channel can be, for example, similar to the microfluidic channel 300 described herein below in conjunction with FIG. 3. The tool shaft 102 can be manufactured from a variety of materials, including metals such as aluminum, stainless steel, or other alloys or metals. In some implementations, the tool shaft 102 can be manufactured from one or more plastics or polymers, such as ethylene chlorotrifluoroethylene (ETCFE), ethylene tetrafluoroethylene (ETFE), fluorinated ethylene propylene (FEP), polychlorotrifluoroethylene (PCTFE), polyether ether ketone (PEEK), perfluoroalkoxy alkanes (PFA), polyphenylene sulfide (PPS), polyphenylsulfone (PPSU), or polysulfone (PSU), among others. The tool shaft 102 can be manufactured to be a narrow shaft with a length that is greater than its overall width, to allow the tip portion 106 to be easily positioned within the ear of a patient. However, it should be understood that other configurations of the tool shaft 102 are possible to facilitate positioning of the handpiece within a desired anatomic structure of a patient.

The angled portion 104 can be angled to facilitate positioning the tip portion 106 within an anatomic structure, such as the round window membrane, of the patient. The angled portion 104 can be manufactured as a separate component of the handpiece 100, such that the angled portion 104 can be attached or detached from the tool shaft 102, as needed. When manufactured as separate materials, the angled portion 104 can be coupled to the tool shaft 102 using a type of connector, such as gaskets, O-rings, snap-on connectors, friction-fit connections, press-fit connections, or Luer lock connections, among others. The angled portion 104 can include a second microfluidic channel in communication with the microfluidic channel of the tool shaft 102, such that fluids or a cannula can be transmitted through the channel of the tool shaft 102, through the angled portion 104, and through the tip portion 106 to an outlet of the tip portion 106. In some implementations, the tool shaft 102 and the angled portion 104 can be manufactured as a single contiguous piece of material or combinations of materials, as described herein.

The angle of the angled portion 104 can be selected based on anatomic features of a patient undergoing a procedure using the handpiece 100. For example, different angles of the angled portion 104 may facilitate the positioning of the tip portion 106 within the ear canal 110. The angled portion can be manufactured from a variety of materials, such as aluminum, stainless steel, or other allows or metals. In some implementations, the angled portion 104 can be manufactured from one or more plastics or polymers, such as ethylene chlorotrifluoroethylene (ETCFE), ethylene tetrafluoroethylene (ETFE), fluorinated ethylene propylene (FEP), polychlorotrifluoroethylene (PCTFE), polyether ether ketone (PEEK), perfluoroalkoxy alkanes (PFA), polyphenylene sulfide (PPS), polyphenylsulfone (PPSU), or polysulfone (PSU), among others. The angled portion 104 can be manufactured to be flexible to a certain degree, to allow for the tip portion to better navigate the ear canal 110 of the patient or the middle ear of the patient. In some implementations, the angled portion 104 is not present, and the handpiece 100 instead comprises a tool shaft 102 and tip portion 106.

The tip portion 106 can be manufactured as part of the tool shaft 102 or as part of the angled portion 104. In some implementations, the tip portion 106 can be detachable from one of the tool shaft 102 or the angled portion 104. In some implementations, any combination of the portions of the handpiece can be manufactured as a single piece. For example, the tip portion 106 and the angled portion 104 can be manufactured as a single piece of one or more materials, the tool shaft 102 and the angled portion 104 can be manufactured as a single piece of one or more materials, or the tool shaft 102 and the tip portion 106 can be manufactured as a single piece of one or more materials (e.g., in implementations when the angled portion 104 is not present). The tip portion 106 can be manufactured from a variety of materials, such as aluminum, stainless steel, or other allows or metals. In some implementations, the tip portion 106 can be manufactured from one or more plastics or polymers, such as ethylene chlorotrifluoroethylene (ETCFE), ethylene tetrafluoroethylene (ETFE), fluorinated ethylene propylene (FEP), polychlorotrifluoroethylene (PCTFE), polyether ether ketone (PEEK), perfluoroalkoxy alkanes (PFA), polyphenylene sulfide (PPS), polyphenylsulfone (PPSU), or polysulfone (PSU), among others.

As depicted in FIG. 1, the tip portion 106 can taper along its length to facilitate positioning through the ear canal 110 of the patient and into the middle ear for delivery of a cannula or other fluid. The tip portion 106 can define a microfluidic channel in a central portion of the tip portion 106, such that fluids transmitted through the microfluidic channel of the tool shaft 102 or the angled portion 104 can be transmitted through the tip portion 106 to an outlet of the tip portion 106. The tip portion can include a collar 108, which can be seated around a grooved region in the tip portion 106 or affixed to the tip portion 106 using a glue or another type of adhesive. In some implementations, the collar 108 is manufactured from the same piece of material as the tip portion 106.

The tip portion 106 can have a shape that is configured to seat with an anatomic structure of a patient, such as the round window 114. The tip portion 106 can have an outlet for the microfluidic channels defined within the tool shaft 102, the angled portion 104, and the tip portion 106, each of which can be in communication with one another. The outlet of the tip portion 106 can be disposed on a needle tip portion of the tip portion 106. The needle tip portion of the tip portion 106 can extend into the cochlea 112 of the patient.

Figure 2:
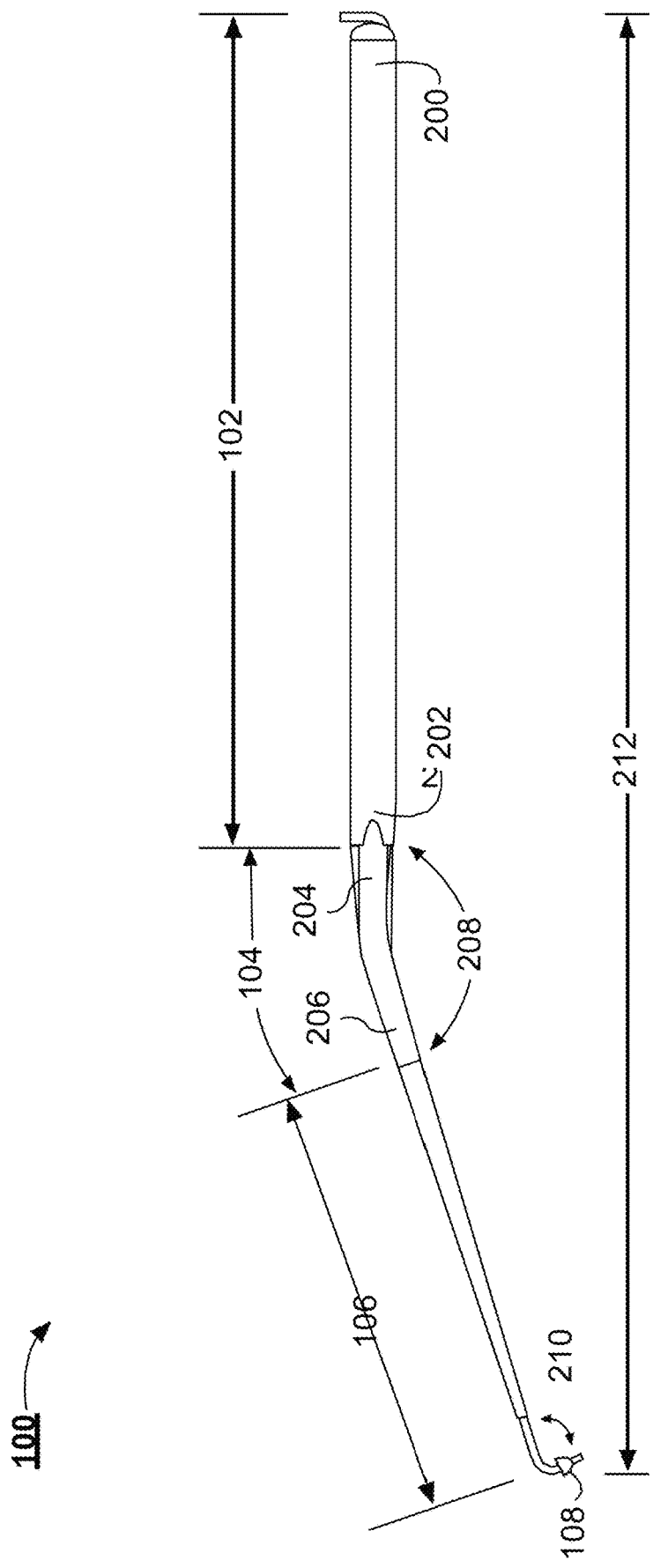
FIG. 2 illustrates a side view of the example handpiece illustrated in FIG. 1, in accordance with one or more implementations.

FIG. 2 illustrates a side view of the example handpiece 100. The handpiece 100 includes the tool shaft 102, the angled portion 104, and the tip portion 106. A surgeon can use the tool shaft 102 to hold and manipulate the handpiece 100 and position of the tip portion 106. The outer surface of the tool shaft 102 can include knurling to enable a better grip of the handpiece 100 by the surgeon. In some implementations, one or more portions of the handpiece 100 can be coupled to a surgical robot. In such implementations, the portions of the handpiece 100 can include fasteners or other coupling devices or structures that can couple handpiece to the surgical robot. The tool shaft 102 can include a proximal end 200 and a distal end 202. The tool shaft 102 can have a diameter of about 4 mm, 5 mm, or about 6 mm. The tool shaft 102 can have a length of between about 90 mm and about 150 mm, between about 90 mm and about 130 mm, or between about 100 mm and about 120 mm. In some implementations, the length of the tool shaft 102 is 110 mm.

The distal end of the tool shaft 102 can be coupled with the proximal end 204 of the angled portion 104. The tip portion 106 is coupled with the distal end 206 of the angled portion 104. The angled portion 104 is angled to enable the tip portion 106 to traverse the ear canal (e.g., the ear canal 110 depicted in FIG. 1) in a minimally invasive procedure and reach the round window or another anatomic structure in the ear of a patient. The angled portion 104 forms an angle 208 between the tool shaft 102 and the tip portion 106. The angle 208 can be about 170° and about 90°, between about 170° and about 110°, between about 170° and about 120°, between about 170° and about 140°, or between about 165° and about 155°. The angle 208 can be defined as the angle between a longitudinal axis of the tool shaft 102 and a longitudinal axis of the tip portion 106. The angle 208 is configured to enable transcanal positing of the tip portion 106 at a round window of a patient. The angle 208 can be selected to enable a surgeon to position the tip portion 106 at the round window and provide the surgeon visual access to the ear canal.

The tip portion 106 can be coupled with the distal end 206 of the angled portion 104. The distal portion of the tip portion 106 can be angle. The angle 210 can be between about 70° and about 140°, between about 75° and about 130°, between about 90° and about 120°, between about 100° and about 120°, or between about 110° and about 120°. For example, the angle 210 can be about 105°, 106°, 107°, 108°, 109°, 110°, 111°, 112°, 113°, 114°, 115°, 116°, 117°, 118°, 119°, or 120°. The angle 210 can be selected to position the distal portion of the tip portion 106 substantially perpendicular to the round window when the handpiece 100 is inserted through the ear canal. The angle 210 can be selected based on the anatomical configuration of an inner or a middle ear of the patient. For example, the surgeon can select a handpiece 100 with an appropriate angle 210 based on the position and angle of the round window and the round window niche. In some implementations, the surgeon can determine which angle 210 to select using CT or MRI images of the middle and inner ear. The handpiece 100 can be manufactured with different angle 210 configurations. In some implementations, the surgeon can bend the tip portion 106 to alter the angle 210 during a procedure.

The tip portion 106 can include a collar 108. The collar 108 can be configured to seat within the round window. For example, the collar 108 can be made of a semi-flexible material that can conform to the round window in the middle ear of a patient, or conform to a different anatomic structure in the ear of the patient. The collar 108 can be rigid enough to prevent more than a desired portion of the handpiece 100 from extending into the cochlea (e.g., the cochlea 112 depicted in FIG. 1) of a patient. The flexible conformability of the collar 108 can form a seal with one or more anatomic structures of the middle ear of a patient. For example, the collar 108 can seal the round window once the tip portion 106 pierces the round window membrane. The collar 108 can also control the depth the end of the tip portion 106 can be inserted into the cochlea. The collar 108 can include a medical-grade silicone, or another type of semi-flexible or biocompatible material. The collar 108 can be substantially domed or semi-spherical in shape. The diameter of the collar 108, at the widest portion, can be between about 0.5 mm and about 3 mm, between about 0.5 mm and about 2.5 mm, between about 1 mm and about 2 mm, or between about 1.5 mm and about 2 mm.

The handpiece 100 can have an overall length 212 between about 130 mm and about 170 mm, between about 140 mm and about 160 mm, or between about 140 mm and about 150 mm. While described as different portions, the tool shaft 102, the angled portion 104, and the tip portion 106 can each be manufactured as single or multiple pieces. For example, the handpiece 100 can include one, two, or three separate pieces. The handpiece 100 can be separable at the interface between any of the tool shaft 102, the angled portion 104, and the tip portion 106. In some implementations, the interface between the tool shaft 102, the angled portion 104, and the tip portion 106 does not indicate that the portions are separable, such as when one or more of the tool shaft 102, the angled portion 104, or the tip portion 106 are formed from a single contiguous piece of material, or when one or more of the tool shaft 102, the angled portion 104, or the tip portion 106 are coupled together permanently or semi-permanently. For example, the tool shaft 102, the angled portion 104, and the tip portion 106 can be manufactured as a single piece. In other implementations, the angled portion 104 and the tool shaft 102 can form a first piece and the tip portion 106 can form a second piece. In some implementations, the handpiece 100 is reusable. In other implementations, the handpiece 100 is disposable. The handpiece 100 can be manufactured from medically-approved sterilizable materials. For example, the handpiece 100 can be manufactured from 316 stainless steel, or any other type of metal described herein, or a sterilizable plastic or polymer as described herein.

Figure 3:
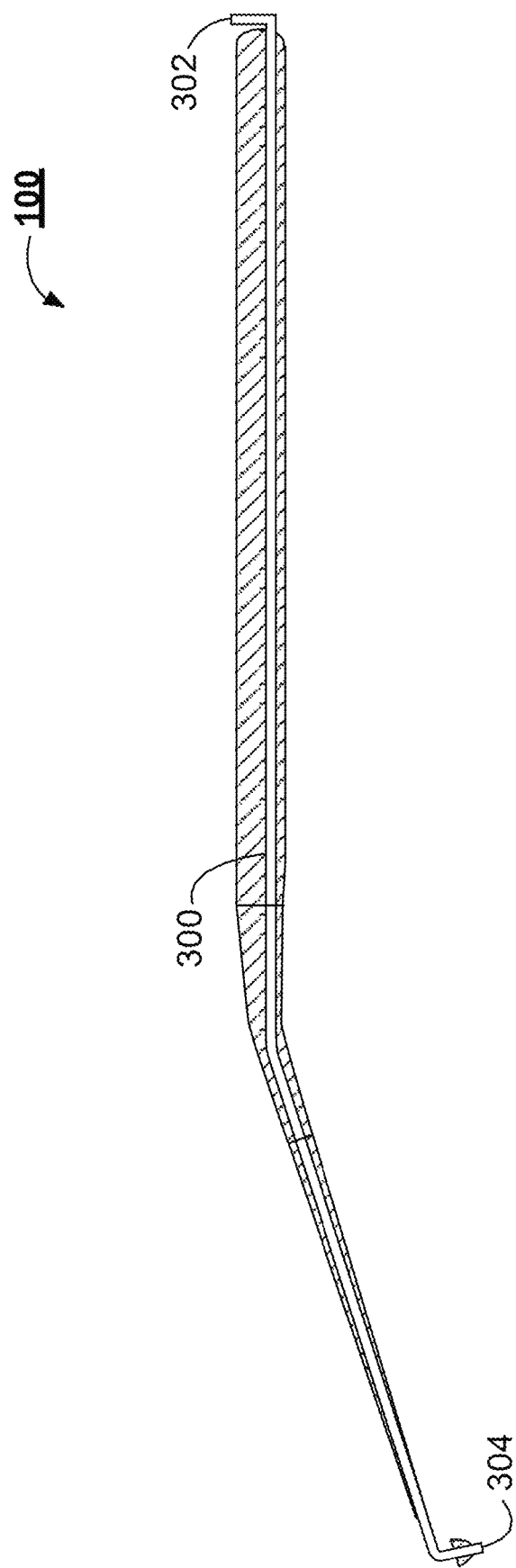
FIG. 3 illustrates a cross-sectional view of the example handpiece illustrated in FIG. 1, in accordance with one or more implementations.

FIG. 3 illustrates a cross-sectional view of the example handpiece 100. The handpiece 100 includes a microfluidic channel 300. The microfluidic channel 300 includes an inlet 302 and an outlet 304. The inlet 302 can be coupled with a reservoir. The reservoir is described further in relation to FIGS. 9 and 10. The microfluidic channel 300 can have a gauge of about 22. The gauge of the microfluidic channel can be between about 12 and 28, between about 16 and about 24, between about 18 and about 22, or between about 20 and 22. The microfluidic channel 300 can have a dead volume of between about 10 µL and about 25 µL, between about 15 µL and about 25 µL, or between about 20 µL and about 25 µL.

Figure 4:
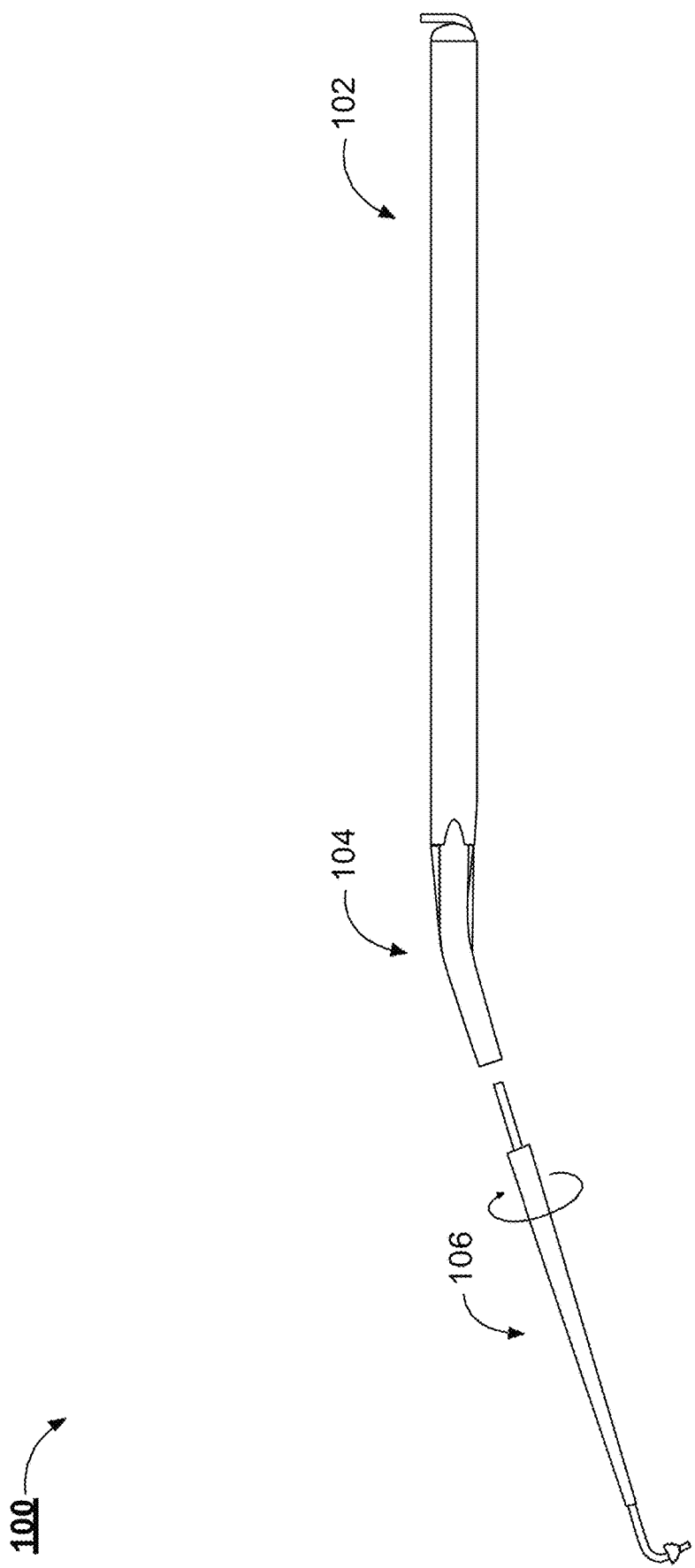
FIG. 4 illustrates a side view of the example handpiece illustrated in FIG. 1, in accordance with one or more implementations.

The microfluidic channel 300 can include different portions. For example, each of the tool shaft 102, angled portion 104, and the tip portion 106 can include a different portion of the microfluidic channel 300. The different portions can be a single channel, continuous channel. In some implementations, the microfluidic channel 300 is separable at the interface between one or more of the portions. In some implementations, the microfluidic channel portions are separable near the interface between the different portions of the handpiece 100. For example, the microfluidic channel portion within the tip portion 106 can extend past the tip portion 106 (as illustrated in FIG. 4) and the microfluidic channel portion within the angled portion 104 can stop prior to the distal end 206, such that portion of the microfluidic channel extending from the tip portion 106 can be received by the angled portion 104. In some implementations, the handpiece 100 can include a plurality of microfluidic channels 300. For example, the handpiece 100 can include different microfluidic channels 300 for delivering different therapeutic agents. In some implementations, a second microfluidic channel 300 can be used to evacuate fluid from the cochlea. The microfluidic channel 300 can be configured to provide or otherwise seat a cannula, such as the cannula 904 described herein in conjunction with FIG. 9, into the cochlea 112 of a patient.

FIG. 4 illustrates a side view of the example handpiece 100. In some implementations, one or more of the portions of the handpiece 100 are separable from one another. FIG. 4 illustrates an example handpiece 100 with a separable tip portion 106. The tip portion 106 can be separated from the tool shaft 102 and the angled portion 104 to facilitate sterilization of the handpiece 100. The tip portion 106 can be separable from the angled portion 104 to enable the tip portion 106 to be recoupled with the angled portion 104 at a different rotational angle. The tip portion 106 can be rotated with respect to the angled portion 104 without separating the tip portion 106 from the angled portion 104. The tip portion 106 can be rotated with respect to the angled portion 104 to provide the surgeon with improved access to the round window. For example, the surgeon, or a surgical robot, can adapt the default position of the tip portion 106 to account for variability between patient anatomies. The handpiece 100 can include gaskets or O-rings at the interface between the separable portions. The separable portions can be coupled together with snap-on connectors, friction-fit or press-fit connections, or Luer lock connections.

Figure 5:
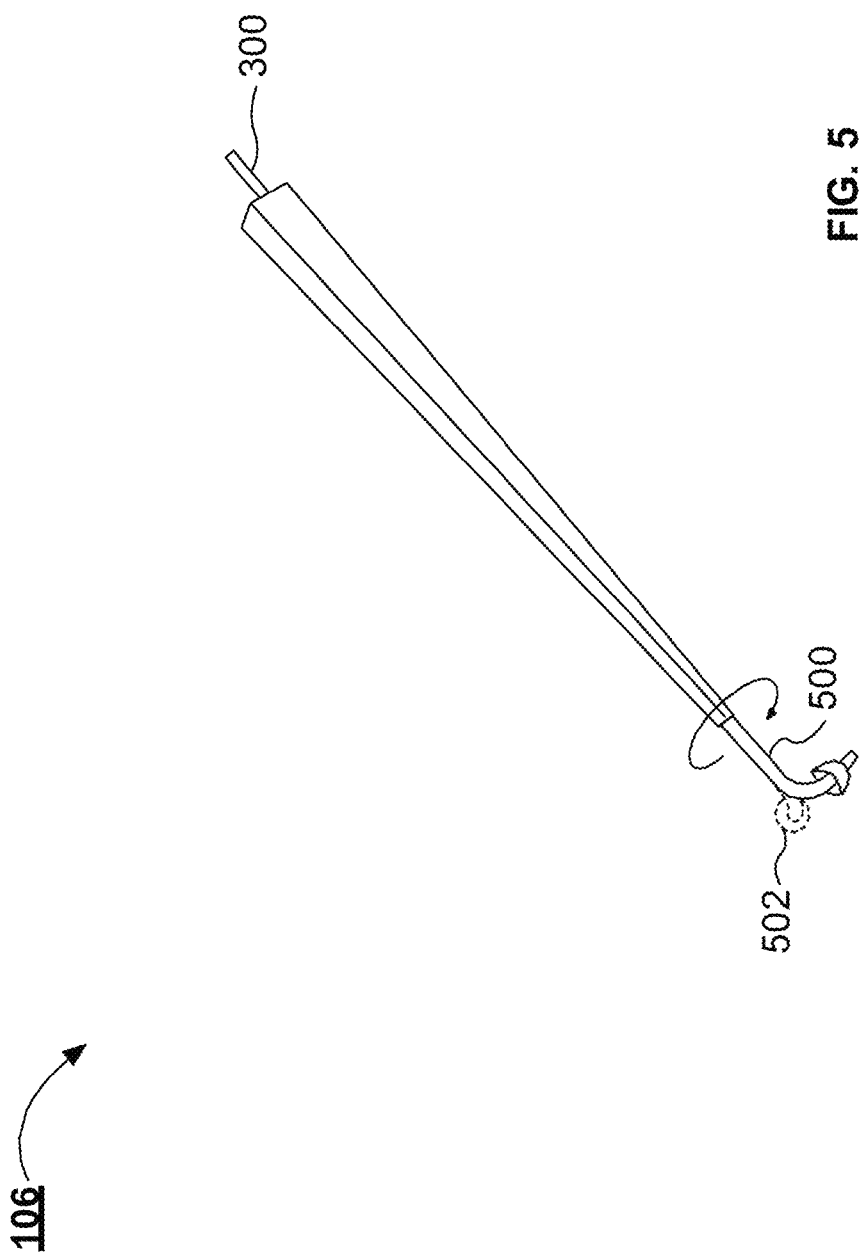
FIG. 5 illustrates an example tip portion for the handpiece illustrated in FIG. 1, in accordance with one or more implementations.

FIG. 5 illustrates an example tip portion 106 for the example handpiece 100. The tip portion 106 illustrated in FIG. 5 is separated from the angled portion 104 and the tool shaft 102 of the handpiece 100. The tip portion 106 can include a tip 500. The tip 500 can be, or can include, a portion of the microfluidic channel 300 extending from the body of the tip portion 106. In some implementations, all of the tip portion 106 can be rotated with respect to the angled portion 104. In other implementations, the tip 500 can be rotated within the tip portion 106. In either example, the tip 500 can be rotated from the position illustrated in FIG. 4 to a second position 502, illustrated by the dashed lines. As shown, the tip portion 500 can be bent or angled to facilitate seating the collar 108 with an anatomic structure in the middle ear of a patient, such as the round window. The bent portion of the tip 500 can form an angle between the outlet of the tip portion and 106 the body of the tip portion 106, where the angle is between about 90 degrees and about 175 degrees.

Figure 6:
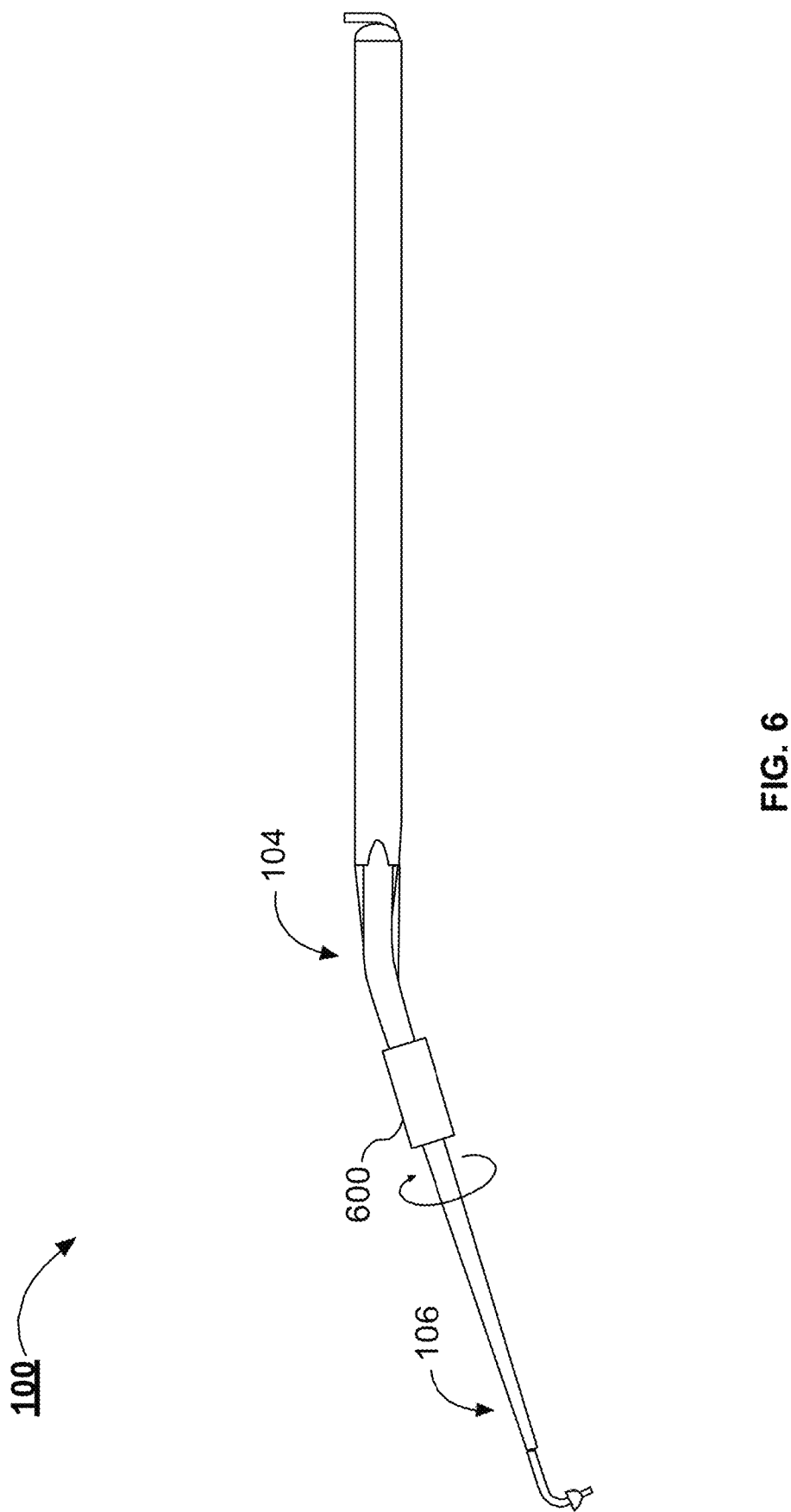
FIG. 6 illustrates an example handpiece with a compression fitting, in accordance with one or more implementations.

FIG. 6 illustrates an example handpiece 100 with a compression fitting 600. The compression fitting 600 can be knurled nut. The compression fitting 600 can couple the angled portion 104 with the tip portion 106. The compression fitting 600 can be loosened to enable the tip portion 106 to rotate with respect to the angled portion 104. Once the surgeon selects a degree of rotation, the surgeon can tighten the compression fitting 600 to lock the degree of rotation between the angled portion 104 and the tip portion 106 in place. In other implementations, the tip portion 106 and the angled portion 104 can be held together with a friction fit that enables the tip portion 106 to be rotated with respect to the tip portion 106. In such implementations, the tip portion 106 and the angled portion 104 can be rotated to a desired degree of rotation, and then pushed into a friction fit portion of the tool shaft 102 to fix the degree of rotation for a surgical procedure. The detachable tip and angled portion allows for the selection of tip materials and dimensions that conform to the anatomic properties of a patient undergoing a procedure using the handpiece 100.

Figure 7:
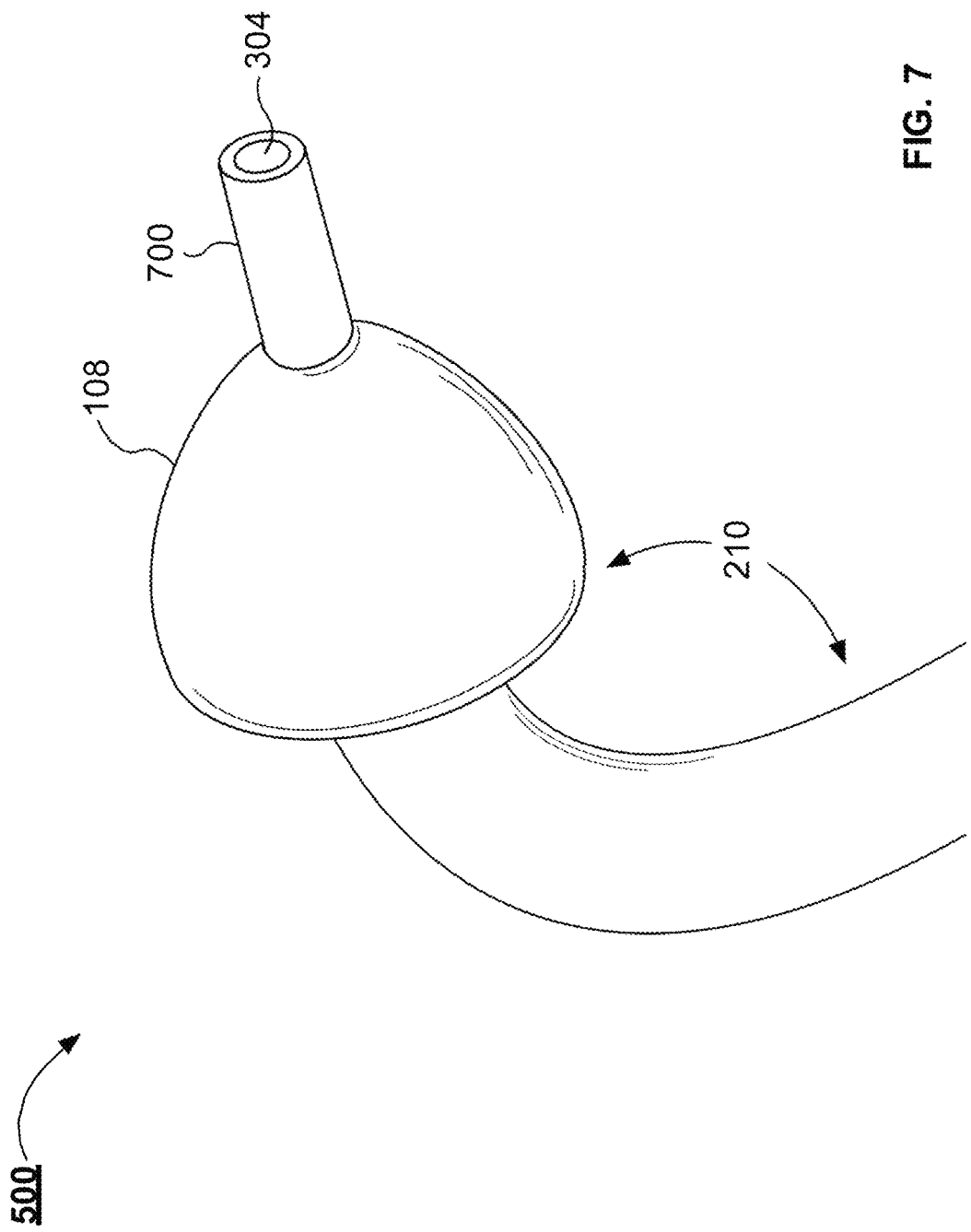
FIG. 7 illustrates an enlarged view of the tip of the example handpiece illustrated in FIG. 1, in accordance with one or more implementations.

FIG. 7 illustrates an enlarged view of the tip 500 of the example handpiece 100. The tip 500 can include a needle end 700. The needle end 700 includes the outlet 304. The needle end 700 can be a blunt end or can be beveled to form a point. The needle end 700 can be configured to pierce the round window membrane or another anatomic structure in the ear of a patient. The needle end 700 can extend past the collar 108 by a length between about 1 mm and about 4 mm, between about 2 mm and about 3 mm, or between about 2.5 mm and about 3 mm. For example, the needle end 700 can have a length of 2.7 mm. The needle end 700 can have a gauge size between about 25 and about 30, between about 26 and about 30, or between about 27 and about 30. Once the collar 108 is seated into the round window only the needle end 700 projects into the cochlea. The collar 108 can control the depth the needle end 700 projects into the cochlea (e.g., the cochlea 112 depicted in FIG. 1, etc.).

The needle end 700 can prevent the needle end 700 from projecting too far into the cochlea. The needle end 700 can prevent the needle end 700 from projected too far into the cochlea and damaging the cochlea. The collar 108 can properly position the outlet 304 within the cochlea so that the therapeutic substance properly disperses through the cochlea (e.g., the cochlea 112 depicted in FIG. 1, etc.). For example, if the outlet 304 is positioned too shallow into the cochlea, the therapeutic substance can concentrate near the round window and not disperse through the cochlea. If the outlet 304 is position too deep into the cochlea, the needle end 700 can cause damage or trauma to the cochlea. In some implementations, the tip 500 is manufactured from a malleable material such that a surgeon can bend the tip 500 to alter the angle 210. The collar 108 can be coupled with the tip 500 with an adhesive. In some implementations, the tip 500 can include a groove in which the collar 108 is seated.

FIGS. 8A and 8B illustrate the tip 500 inserted into the round window. FIG. 8A illustrates the handpiece 100 inserted through the ear canal with the tip 500 inserted into the round window 114, or another type of anatomic structure in the ear of a patient. FIG. 8B illustrates an enlarged view, from FIG. 8A, of the tip 500 inserted into the round window 114. The tip 500 can be used to pierce the round window membrane. The tip 500 can be inserted into the round window 114. The collar 108 can be seated into the round window 114 and seal the round window 114 as fluid is injected into the cochlea 112. The collar 108 is tapered from a diameter smaller than the diameter of the round window 114 to a diameter that is wider than the diameter of the round window 114. When the collar 108 is depressed against the round window 114, the collar 108 can occlude the round window 114. The collar 108 can also be used to control the insertion depth of the tip 500 into the cochlea 112. For example, the collar 108 can prevent the tip 500 from being inserted into the cochlea past the collar 108. The portion of the collar 108 with a diameter wider than the diameter of the round window 114 can substantially stop the tip 500 from farther insertion of the tip 500 into the cochlea 112. Moving the collar 108 towards the outlet 116 of the tip 500 reduces the depth to which the tip 500 can be inserted. The collar 118 can prevent the tip 500 from being inserted too far into the cochlea 112.

Figure 9:
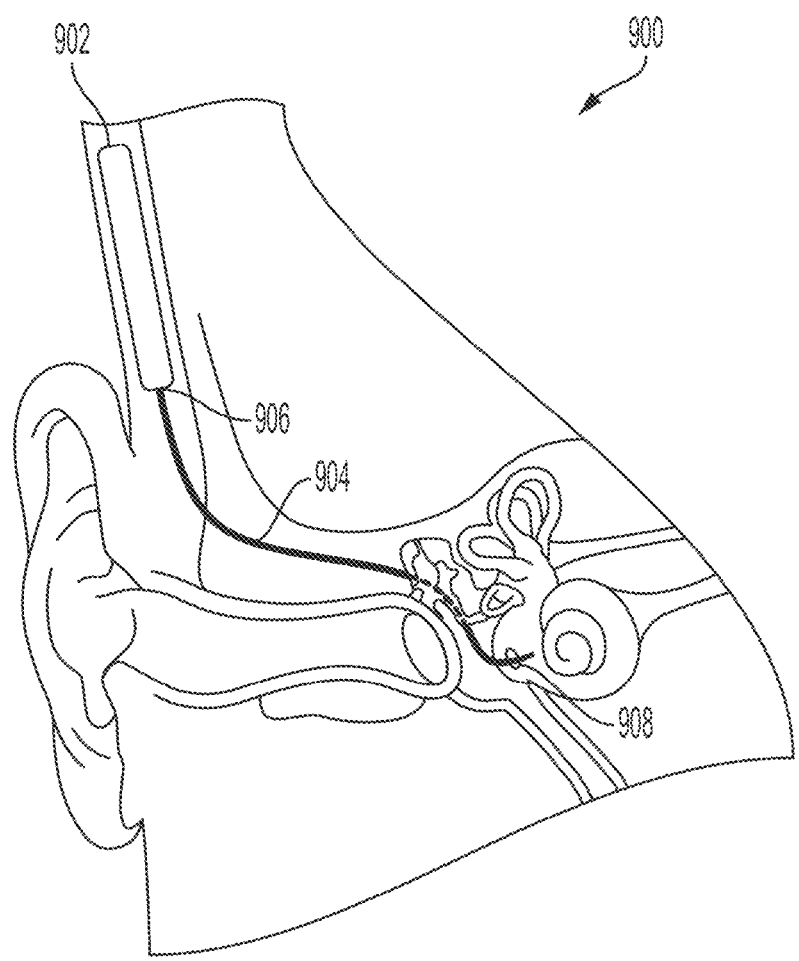
FIG. 9 illustrates an example system to inject compounds into the inner ear, in accordance with one or more implementations.

FIG. 9 illustrates an example system 900 to inject compounds into the inner ear. The system 900 can include a micropump 902. The system 900 can include a cannula 904. The cannula 904 can also be referred to as a catheter 904. The cannula 904 can be coupled with the outlet 906 of the micropump 902. The cannula 904 can be inserted through the round window membrane 908 and into the inner ear. The cannula 904 can be inserted through the round window membrane 908 using the handpiece 100 described herein above.

Figure 10:
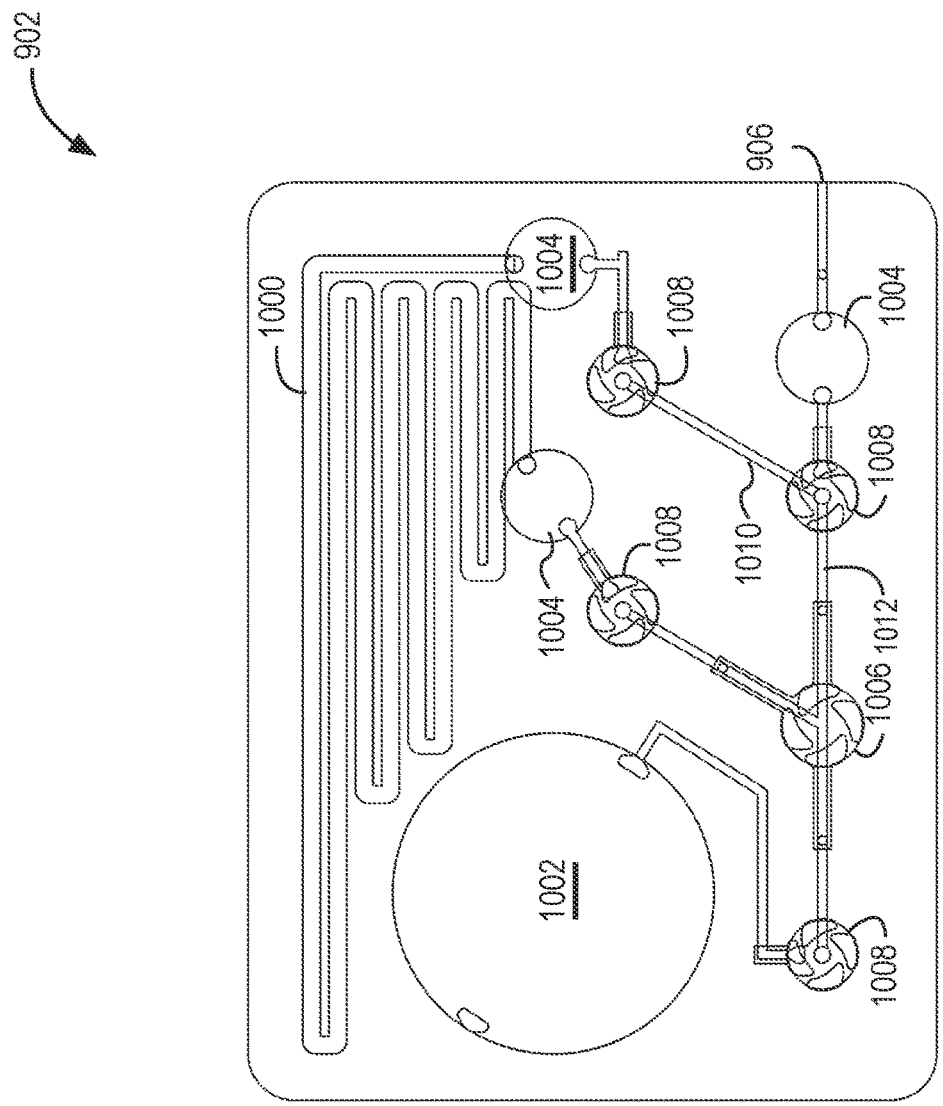
FIG. 10 illustrates a top view of an example micropump for use in the example system illustrated in FIG. 9, in accordance with one or more implementations.

The micropump 902 is described further in relation to FIG. 10, among others. As an overview, the micropump 902 can be a reciprocating, automated fluid injection system. The micropump 902 can include an integrated drug reservoir. The drug stored in the drug reservoir can be referred to as a compound and the drug reservoir can be referred to as a compound reservoir. The micropump 902 can dispense the compound from the compound reservoir to the inner ear, via the cannula 904, at predetermined intervals. The micropump 902 can be configured to both inject the compound into the inner ear and to withdraw fluid from the inner ear so that the net volume added to the inner ear is substantially zero. The micropump 902 can include one or more internal pumps and valves that can control the withdrawal and infusion fluid to and from the micropump. For chronic delivery applications, the micropump 902 can be worn around the head or implanted. For example, as illustrated in FIG. 9, the micropump 902 can be housed in a sealed housing and implanted under the scalp behind or near the ear.

The system 900 also includes the cannula 904. The cannula 904 can include a sharp, smooth tip. For example, the tip of the cannula 904 can include a sharpened bevel. The sharp, smooth tip can enable the cannula 904 to pierce the round window membrane 908. In some implementations, the sharp, smooth tip can enable the cannula 904 to pierce the round window membrane 908 without collapsing the round window membrane 908. The cannula 904 is described further in relation to FIG. 11, among others.

FIG. 10 illustrates a top view of an example micropump 902. The micropump 902 can include a drug reservoir 1000 and a fluid storage capacitor 1002. A drug-containing fluid can be dispensed from the micropump 902 via the outlet 906. The micropump 902 can include a pump 1006. The micropump 902 can include a plurality of valves 1008 and fluid capacitors 1004.

The micropump 902 can be a multilayered device. The micropump 902 can include fluid routing layers. For example, the fluid routing layers can include the drug reservoir 1000, fluid storage capacitor 1002, fluid capacitors 1004, the channels 1010, and a loading chamber 1012. The micropump 902 can include one or more active layers. The active layers can include the actuators of the valves 1008 and the pump 1006, the controller that controls the valves 1008 and the pump 1006, and a power source for powering the micropump 902. The fluid routing layers can be separated from the active layers by a membrane. The fluid routing layers can include polyetherimide (PEI). The membrane separating the fluid routing layer and the active layers can include a flexible membrane, such as polyimide and Viton.

The micropump 902 can include the drug reservoir 1000. The drug reservoir 1000 can be machined (e.g., laser etched) into one or more of the fluid routing layers. The drug reservoir 1000 can be configured as a serpentine or other channel structure. The drug reservoir 1000 can be configured as a channel with an inlet and an outlet such that a fluid can be pumped into the inlet to force the drug from the outlet of the drug reservoir 1000 and into one of the channels 1010. The drug reservoir 1000 can have a channel width between about 300 µm and about 1200 µm, between about 400 µm and about 1000 µm, between about 500 µm and about 900 µm, between about 600 µm and about 800 µm, or between about 700 µm and about 800 µm. The drug reservoir 1000 can have a channel height between about 300 µm and about 1200 µm, between about 400 µm and about 1000 µm, between about 500 µm and about 900 µm, between about 600 µm and about 800 µm, or between about 700 µm and about 800 µm. The drug reservoir 1000 can have a total channel length between about 300 mm and about 100 mm, between about 300 mm and about 800 mm, or between about 300 mm and about 600 mm.

The micropump 902 can include a fluid storage capacitor 1002. The fluid storage capacitor 1002 can be a cylinder formed in the fluid routing layer. The fluid storage capacitor 1002 can have a diameter of between about 10 mm and about 20 mm, between about 12 and about 18 mm, or between about 14 and about 16 mm. The fluid storage capacitor 1002 can be configured to store fluid withdrawn from the inner ear of the patient. The fluid storage capacitor 1002 can also provide fluid to the inlet of the drug reservoir 1000 to force the drug out of the outlet of the drug reservoir 1000.

The micropump 902 can also include a plurality of fluid capacitors 1004. The fluid capacitors 1004 can be machined in line with the fluid channels 1010 and loading chamber 1012 of the fluid routing layer. The fluid capacitors 1004 can have a diameter of between about 2 mm and about 10 mm, between about 2 mm and about 8 mm, between about 2 mm and about 6 mm, or between about 4 mm and about 6 mm. The fluid storage capacitor 1002 and the fluid capacitors 1004 can have a ceiling formed by the membrane separating the fluid routing layers and the active layers.

The fluid capacitors 1004 can improve power efficiency, help to regulate peak flow rates, and provide fluid storage. For example, the channels 1010 of the micropump 902 can have relatively high fluid resistances, which can cause a relatively large time constant associated with expelling fluid from the micropump 902. Accordingly, with a relatively large time constant, the valves 208 may need to be powered for several seconds to open the valves and to enable the pump chamber to have time to fully drain or fill. The fluid capacitors 1004 that are in line with the fluid channels 1010 have lower fluid resistance and can enable relatively fast transfer of fluid into and out of the pump chamber followed by passive fluid flow associated with the pressure equilibration of the fluid capacitors 1004. This can reduce the amount of time valves 208 are held open (to on the order of tens of milliseconds) and can reduce power consumption. The fluid capacitors 1004, for example the fluid capacitor 1004 near the outlet 906, can attenuate flow rate bursts generated by pump strokes and reduce large peak flow rates.

The micropump 902 can include one or more pumps 1006. The pump 1006 can include an actuator in the active layers of the micropump 902. The actuator can hold electromagnets in place. When the electromagnets are unpowered, springs can keep the actuator heads pressed against the polyimide membrane. Pressure against the polyimide membrane presses the Viton layer against an opening to the cylinder of the valve 1008 formed in the fluid layer and forms a fluidic seal that closes the valve of the pump 1006.

Cycling the actuator of the pump 1006 can result in fluid displacement in the fluid chamber of the pump 1006. The valves 1008 can be cycled (e.g., opened or closed) to control the direction of the fluid flow through the micropump 902. For example, for each stroke type, one valve can act as an intake valve and another valve can act as an expulsion valve. At the beginning of a pump stroke, the intake valve opens, and then the pump actuator is powered resulting in fluid being drawn into the pump chamber from an adjacent fluidic capacitor. Next, the intake valve closes. Then the expulsion valve opens, followed by deactivation of the pump actuator, resulting in fluid being pushed out of the pump chamber into a different fluidic capacitor. Finally, the expulsion valve closes. Depending on which valves are chosen as the intake and expulsion valves, the pump can produce three different types of pump strokes: infusion (e.g., fluid is pumped out of the micropump 902), withdrawal (e.g., fluid is pumped from an external source into the micropump 902), and drug refresh or priming (e.g., fluid is pumped into the loading chamber 1012 to be pumped out of the micropump 902 at the end infusion stroke).

The micropump 902 can include one or more valves 1008. The valves 1008 can have a construction similar to the pump 1006. For example, the valves 1008 can include a cylinder chamber formed into the fluidic layers. The valves 1008 can include an actuator in the active layers that holds electromagnets in place. When the electromagnets are unpowered, the valves can be held in a closed position by a spring that forces the actuator against the membrane to form a seal in the opening of the cylinder chamber of the valve 1008. Activation of the actuator can force the electromagnets against the spring and away from the membrane to enable fluid to flow through the valve 1008.

Figure 11:
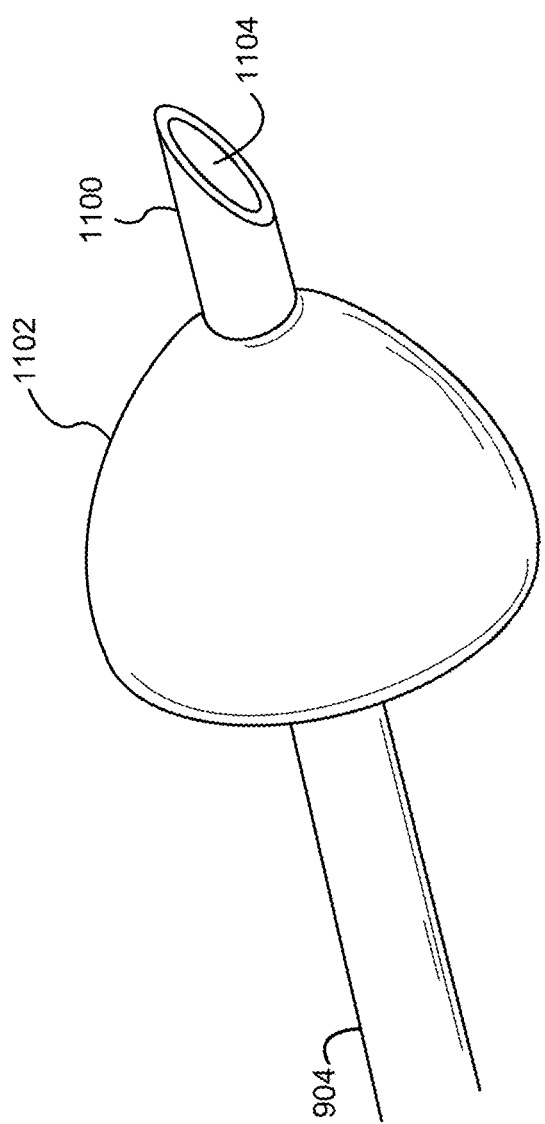
FIG. 11 illustrates an example tip of a cannula that can be used in the example system illustrated in FIG. 9, in accordance with one or more implementations.

FIG. 11 illustrates an example tip 1100 of the cannula 904. The cannula 904 can include the tip 1100 and a stopper 1102, which may also be referred to in this disclosure as a bleb 1102. The tip 1100 can include an outlet 1104 that enables fluid to flow into and out of the tip 1100 and cannula 904.

The cannula 904 can include a plurality of different materials. The cannula 904 can include a plurality of different portions and each of the different portions can include a different material. For example, a first portion of the cannula 904 can include polyetheretherketone (PEEK) tubing. The first portion of the cannula 904 can couple with the micropump 902. The first portion of the cannula 904 can be between about 2 cm and about 10 cm, between about 2 cm and about 8 cm, or between about 3 cm and about 6 cm. The first portion of the cannula 904 can have an inner diameter (ID) between about 50 µm and about 300 µm, between about 100 µm and about 200 µm, or between about 150 µm and about 200 µm.

The cannula 904 can include a second portion. The second portion can include the tip 1100. The second portion can include Polytetrafluoroethylene (PTFE) tubing. The second portion can be between about 1 cm and about 5 cm, between about 2 cm and about 5 cm, or between about 3 cm and about 5 cm in length. In some implementations, the first and second portion of the cannula 904 can be coupled together by Tygon® tubing. The cannula 904 can be introduced to a cochlea of a patient, such the cochlea 112 shown herein above in FIG. 1, using the handpiece 100. Introduction of the cannula 904 to a patient using the handpiece 100 is described in further detail herein below.

The tip 1100 can have an outer diameter of between 10 µm and 200 µm, between about 10 µm and about 150 µm, or between about 50 µm and about 100 µm. The tip 1100 can have an inner diameter between 5 µm and about 200 µm, between about 15 µm and about 150 µm, or between about 50 µm and about 110 µm. The tip 1100 can be narrow enough to be provided via one or more of the channels defined in the portions (e.g., the tool shaft 102, the angled portion 104, or the tip portion 106, etc.) of the handpiece 100.

The tip 1100 can include a bevel that enables the tip 1100 to pierce the round window membrane. The angle of the bevel can be between about 10 degrees and about 45 degrees, between about 15 degrees and about 45 degrees, or between about 25 and about 45 degrees. In some implementations, the bevel is 30 degrees. The bevel can form a point or a sharp edge that can be used to pierce one or more anatomic structures in the ear of a patient.

The tip 1100 can be inserted through the round window membrane 908 (e.g., using the handpiece 100, etc.) such that the tip 1100 of the cannula 904 bathes in the perilymphatic fluid of the scala tympani. The tip 1100 can have a hardness (or stiffness) that is substantially greater than the body of the cannula 904. The stiffened tip 1100 can facilitate penetration of the round window membrane 908. In some implementations, the cannula 904 is bent at an angle that substantially matches the middle ear anatomy to facilitate insertion through the round window membrane 908. In some implementations, the bend in the cannula 904 can be near the tip 1100.

The tip 1100 can penetrate several millimeters into the scala tympani. For example, the tip 1100 can penetrate between about 1 mm and about 5 mm or between about 1 mm and about 3 mm into the scala tympani. The tip 1100 can include a stopper 1102 (also referred to as a bleb 1102) that can prevent the tip 1100 from penetrating too deep into the scala tympani. For example, the stopper 1102 can be positioned about 3 mm from the end of the tip 1100 such that the tip 1100 is positioned 3 mm into the scala tympani when the stopper 1102 comes into contact with the round window membrane 908. In some implementations, the stopper 1102 can help create a seal between the cannula 904 and the round window membrane 908 to substantially prevent fluid leak from the inner ear.

The tip 1100 can be coated with a soft, silicone-like material that seals against the round window membrane 908 following insertion through the round window membrane 908. The cannula 904 can be flexible to facilitate insertion through the round window membrane 908 during surgical procedures. The cannula 904 can be locked within the middle ear space to prevent movement of the cannula 904 after implantation.

The cannula 904 can be coated with a material that releases anti-inflammatory compounds to control middle ear infection. For example, the cannula 904 can be coated with dexamethasone and/or methylprednisolone. In some implementations, the cannula 904 can remain in place for several weeks or months. In other implementations, the cannula 904 can be used acutely and then removed.

Figure 12:
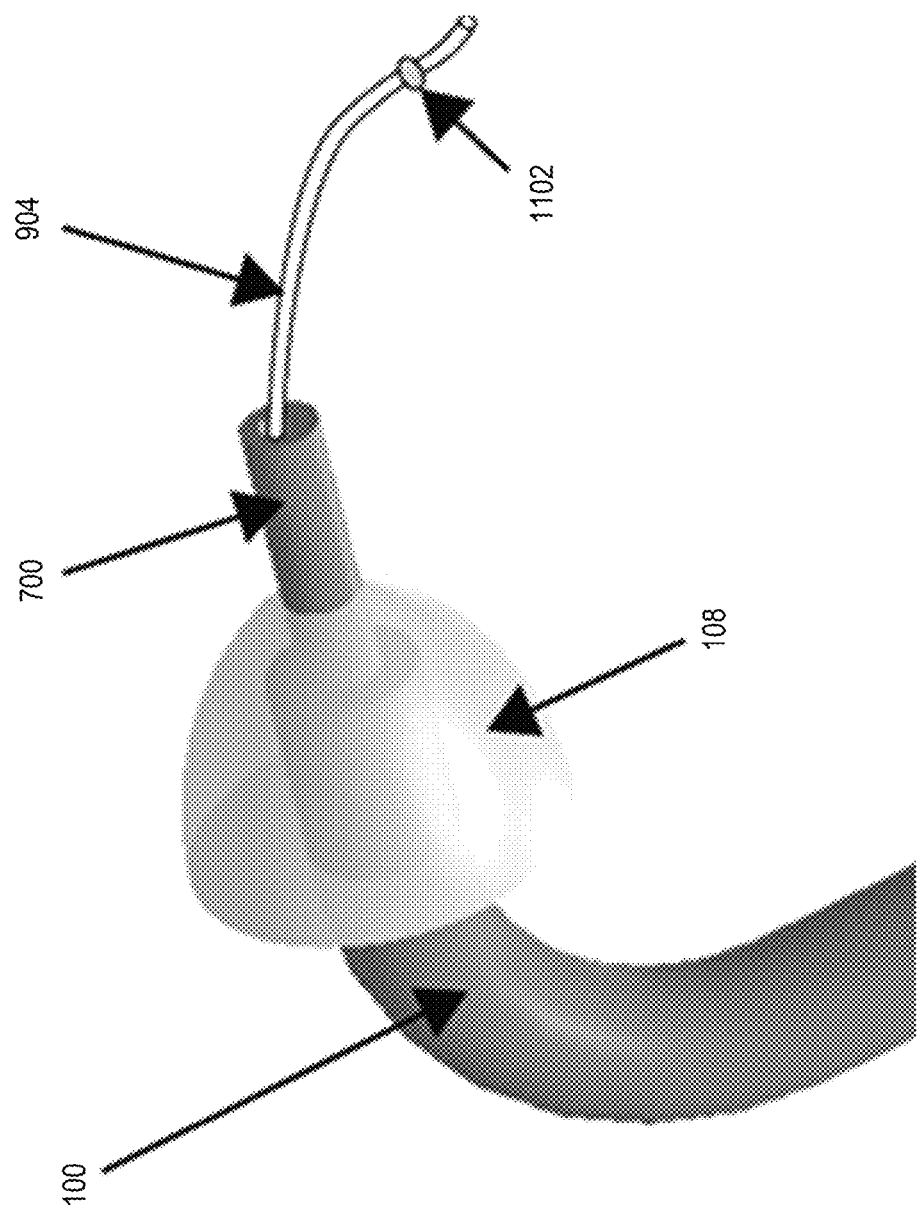
FIG. 12 depicts the example handpiece of FIG. 1 together with the example cannula of FIG. 9 in an arrangement that can be used to facilitate seating the cannula within the round window membrane of a patient, in accordance with one or more implementations.

FIG. 12 depicts the example handpiece 100 of FIG. 1 together with the example cannula 904 of FIG. 9 in an arrangement that can be used to facilitate seating the cannula 904 within the round window membrane of a patient. As shown, the cannula 904 can be positioned within the channel defined by the handpiece 100. For example, a user (e.g., a surgeon) can thread the cannula 904 through the handpiece 100 to that a portion of the cannula 904, as well as the stopper 1102, protrudes through the needle end 700 of the handpiece 100. Threading the cannula 904 through one or more of the channels of the handpiece 100 can allow the cannula 904 to be introduced to an anatomic structure of a patient, such as the round window membrane of the middle ear. In some implementations, the cannula 904 can be held in place in tip portion 600 of the handpiece 100, until released by a surgeon or surgical robot. The cannula 904 can be released, for example, once the collar 108 of the handpiece 100 is seated against the round window of the patient.

In some implementations, the materials and dimensions of the handpiece 100 and the cannula 904 can be selected to facilitate threading the cannula 904 through the handpiece 100 to achieve the arrangement shown in FIG. 12. For example, the cannula 904 can be made from a flexible, biocompatible polymer, such as poly(tetrafluoroethylene) (PTFE), thereby allowing the 904 to be bent and threaded through the handpiece 100. The tubing that forms the cannula 904 can have an outer diameter that is smaller than the inner diameter of the channel defined by the handpiece 100. In some implementations, the stopper 1102 can also be positioned at a predetermined distance from an end of the cannula 904. For example, the predetermined distance may be in the range of about 1 millimeter to about 3 millimeters.

In operation, the cannula 904 can be threaded through the handpiece 100, and then the handpiece 100 can be used to pierce the round window membrane. The collar 108 at the end of the handpiece 100 can help to seat the handpiece 100 correctly in the round window membrane, as described above. The cannula 904 can be pushed out the needle end 700 of the handpiece 100 and through the round window membrane after the needle end 700 of the handpiece 100 has pierced the round window membrane. The handpiece 100 can then be pulled away from the middle ear, while the cannula 904 remains behind due to friction between the cannula 904 and the round window membrane. Thus, the friction can hold the cannula 904 in place within the round window membrane. The cannula 904 can remain in the middle or inner ear even after the handpiece 100 is completely withdrawn from the patient, and thus the handpiece 100 can accurately seat the cannula 904 in a desired region of the ear of a patient. The stopper 1102 can be used to control the distance to which the cannula 904 protrudes into the inner ear. In some implementations, the stopper 1102 can be used to control the distance to which the cannula 904 protrudes into an anatomic structure of a patient, such as a cochlea (e.g., the cochlea 112 shown in FIG. 1, etc.). In some implementations, the stopper 1102 can be positioned in the inner ear. In some other implementations, the stopper 1102 can be positioned in the middle ear.

Figure 13:
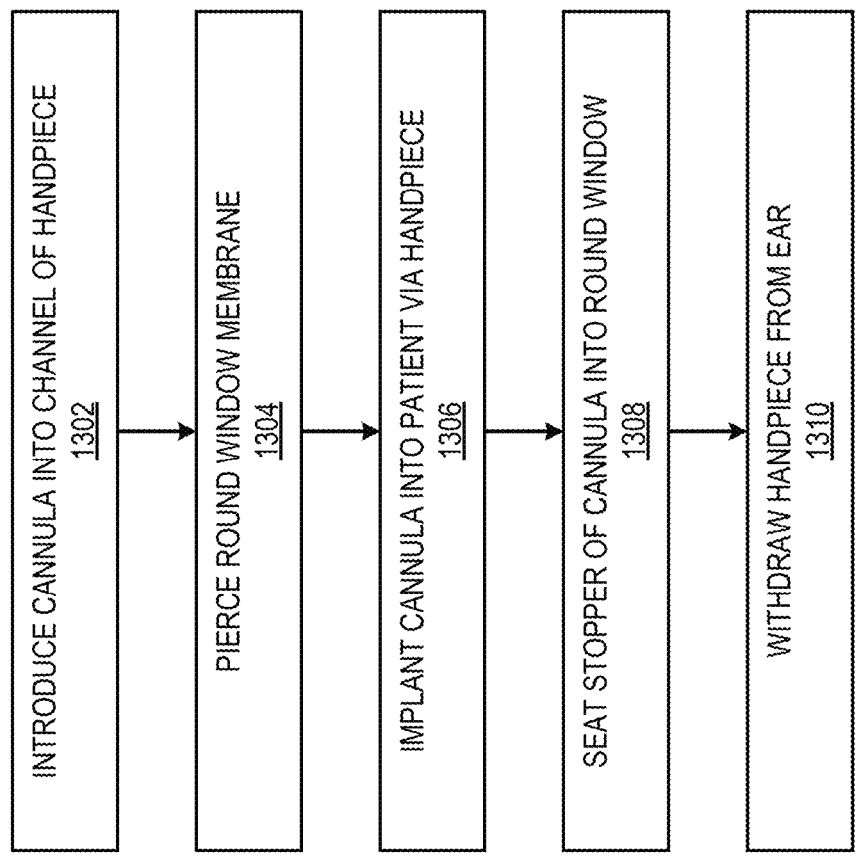
FIG. 13 illustrates a block diagram of an example method to flow fluid into the inner ear of a patient using the example system illustrated in FIG. 9, in accordance with one or more implementations.

FIG. 13 illustrates a block diagram of an example method 1300 to flow fluid into the inner ear of a patient. The method can be performed, for example, by a surgeon utilizing a handpiece (e.g., the handpiece 100 described herein, etc.), or a surgical robot utilizing a handpiece. The method 1300 can include introducing a cannula into a channel of a handpiece (BLOCK 1302). The method 1300 can include piercing a round window membrane of a patient (BLOCK 1304). The method 1300 can include implanting the cannula in the patient via the handpiece (BLOCK 1306). The method 1300 can include seating a stopper in the round window (BLOCK 1308). The method 1300 can include withdrawing the handpiece from the ear of the patient (BLOCK 1310).

The method 1300 can include introducing a cannula (e.g., the cannula 904, etc.) into a channel of a handpiece (BLOCK 1302). Referring also to FIGS. 9-12, the cannula can be the cannula 904 and the handpiece can be the handpiece 100, as described above. The cannula 904 can be formed from a flexible material, such as PTFE, that allows the cannula 904 to be maneuvered into the channel of the handpiece 100. In some implementations, the cannula 904 can be threaded into the channel of the handpiece 100. The cannula 904 can be inserted into the channel to a distance that allows an end of the cannula 904 to be positioned at or near an outlet of the channel of the handpiece 100 (e.g., at or near a tip portion of the handpiece 100). In some implementations, the cannula 904 can protrude out from the needle portion 700 of the handpiece 100 (e.g., as depicted in FIG. 12, etc.). In some implementations, the cannula 904 can remain within the needle portion 700 of the handpiece 100, until the handpiece 100 is properly seated against an anatomic structure of a patient (e.g., the round window of the middle ear, etc.).

The method 1300 can include piercing a round window membrane, or another anatomic structure within the middle or inner ear, of a patient (BLOCK 1304). In some implementations, the round window membrane or other anatomic structure can be pierced with the tip portion of the handpiece 100. For example, the provided handpiece 100 can be inserted through the ear canal (e.g., the ear canal 110 as depicted in FIG. 1, etc.). While the handpiece 100 is inserted, the cannula 904 can remain inside the channel of the handpiece 100. The angled portion 104 of the handpiece 100 can be configured to enable transcanal access of the round window. The tip 500 of the tip portion 106 can be angled to position the needle end 700 substantially perpendicular to the round window and round window membrane, or another anatomic structure within the ear of a patient. The needle end 700 can be pressed against the round window membrane to pierce the round window membrane. In some implementations, the needle end 700 can be pressed against another anatomic structure within an ear of a patient to pierce the anatomic structure. The collar 108 can prevent the needle end 700 from projecting too far into the cochlea, or other inner ear organ or anatomic structure, and causing damage to the cochlea or said other anatomic organ. However, the collar 108 can allow the needle end 700 to project far enough into the round window membrane, or other anatomic structure, to introduce and affix the cannula 904 to the patient.

The collar 108 can seat into the round window, or another anatomic structure within the ear of a patient, to seal the round window as the fluid is injected into the cochlea. Based on the anatomy of the patient, a surgeon can set a rotational offset between the tip portion and the angled portion of the handpiece 100 to enable the needle end 700 to access the round window. Also based on the anatomy of the patient, the surgeon can set the angle 210 between the needle end 700 and the tip portion such that the outlet 304 is positioned substantially perpendicular to the round window and round window membrane. CT or MRI scans of the middle and inner ear of the patient can be conducted. The surgeon can measure the anatomical angles of the inner and middle ear of the patient to select the angle 210 of the tip portion 106. Also, based on the CT or MRI scans the surgeon can select the length of the needle end 700 such that when the collar 108 is seated into the round window the outlet 304 is properly positioned within the cochlea. The proper position of the outlet 304 can be a depth into the cochlea that does not cause damage to the cochlea but enables distribution of the fluid through the cochlea.

The method 1300 can include implanting the cannula in the patient via the handpiece (BLOCK 1306). The cannula 904 can be implanted via an outlet of the handpiece 100. For example, the cannula 904 can be pushed out from the needle end 700 of the handpiece 100 that was used to pierce the round window membrane, and can be inserted through the round window membrane. In some implementations, the length to which the cannula 904 is inserted can be controlled based on the position of the stopper 1102. Alternatively, the cannula 904 could be inserted manually without the use of the handpiece 100. For example, another tool could be used to pierce the round window membrane before the cannula 904 is inserted, or the cannula 904 itself could be used to pierce the round window membrane. However, such an approach can be challenging to implement, and may require a surgically invasive procedure to provide visual and spatial access to the middle ear. In addition, the handpiece 100 itself could be used to administer drugs or other therapeutic substances without the use of the cannula. However, doing so would not be compatible with chronic drug delivery. Use of the cannula with the handpiece can address both of these technical challenges.

The method 1300 can include seating the stopper in the round window (BLOCK 1308). Also referring to FIG. 11, among others, the cannula 904 can include a stopper 1102. The stopper 1102 can be cone-shaped and can be configured to seat within the round window or the piercing made in the round window membrane made by the tip 1100. Seating the stopper 1102 in the round window membrane can project the tip 1100 into the inner ear a predetermined length. In some other implementations, the cannula 904 does not include a stopper 1102 and the cannula 904 can be held in place once the tip 1100 pierces the round window membrane with a silicone-based glue.

The method 1300 can include withdrawing the handpiece 100 from the ear of the patient (BLOCK 1310). The handpiece 100 can be carefully withdrawn so as not to disturb the implanted cannula. Thus, removal of the handpiece 100 can leave the cannula behind. The cannula 904 can remain within the inner ear on a permanent or semi-permanent basis. As described herein above, the cannula 904 can be seated in the round window membrane, or another anatomic structure, in the ear of a patient. In some implementations, the cannula 904 can be seated in the middle ear of a patient. In some implementations, the cannula 904 can be seated in the inner ear of the patient. A portion of the cannula 904 (e.g., the tip 1100 having the outlet 1104, etc.) can extend into an anatomic organ or structure in the inner ear, such as the cochlea (e.g., such the cochlea 112 depicted in FIG. 1, etc.).

The cannula 904 may be compatible with chronic drug delivery. For example, the cannula 904 can remain implanted in the patient for a long period of time. In some implementations, the method 1300 can also include implanting a micropump into the patient. Referring also to FIGS. 9-11, the micropump can be the micropump 902 illustrated in FIGS. 9 and 10. Implanting the micropump 902 can include performing an additional surgical procedure to implant the micropump in a region near the skull of the patient, as depicted in FIG. 9. Implanting the micropump 902 can include coupling the micropump to a microchannel that is in fluid communication with the outlet 1104 of the tip 1100 of the cannula 904. Thus, the micropump 902 can pump fluid, such as fluid from a drug reservoir, through the microchannel, the cannula 904, and into the cochlea or other organ in the inner ear of a patient. As the micropump 902 and the 904 can be implanted on a permanent or semi-permanent basis, continuous or long-term drug delivery is possible.

The micropump 902 can include a drug reservoir 1000 for the storage of drugs or other fluids to be injected into the inner ear of the patient. The micropump 902 can include a fluid storage capacitor 1002. After injecting fluid into the inner ear, the micropump 902 can withdraw fluid from the inner ear and store the fluid in the fluid storage capacitor 1002 such that the net fluid displacement from the injections by the micropump 902 is substantially zero for a cycle that includes an injection phase and a withdrawal phase. The micropump 902 can include a pump 1006 that can pump fluid from the drug reservoir 1000 into the inner ear and that can withdraw fluid from the inner ear for storage in the fluid storage capacitor 1002. Maintaining the net fluid displacement at near-zero can prevent the creation of surplus pressure in the inner ear and potential damage to anatomic structures therein.

In some implementations, the method 1300 can include flowing a fluid into the inner ear. Flowing the fluid into the inner ear can include priming the micropump 902, infusing the fluid into the inner ear, and then withdrawing fluid from the inner ear. For example, to prime the micropump 902, a first valve 1008 coupled with the first end of the drug reservoir 1000 can be opened and the pump 1006 can be activated to draw the drug-containing fluid from the drug reservoir 1000 into a loading chamber coupled with the outlet 906. Once the first valve 1008 is closed, a second valve 1008 coupled with the second end of the drug reservoir 1000 can be opened to the fluid previously in the loading chamber (and displaced by the drug-containing fluid) into the opposite end of the drug reservoir 1000 from which the drug-containing fluid was drawn. To infuse the drug-containing fluid into the inner ear, fluid can be pumped from the fluid storage capacitor 1002 toward the outlet 906, which can force the drug-containing fluid in the loading chamber out through the outlet 906. After the drug has been allowed to diffuse for some time in the inner ear, the micropump 902 can withdraw a volume of fluid from the cochlea. The withdrawn volume can be substantially the same volume as the volume of the drug infused into the cochlea. In some implementations, an additional compound or drug can be introduced into the drug reservoir 1000 from an external reservoir when the level of compound in the drug reservoir 1000 falls below a predetermined level.

The above-described methods can also be used to inject large or lipophobic compounds that may not be suitable for delivery to the inner ear via other methods. For example, other methods may deliver these compounds to the inner ear by placement of these compounds within a liquid or gel formulation. The formulation can then be placed on the round window membrane. The compound can pass into the cochlea via passive transport through the round window membrane. This transport mechanism may not be effective for large or lipophobic drugs, and such drugs can only pass through the round window membrane through slow, active transport mechanisms. Also, the pharmacokinetics of trans-round window membrane delivery may be difficult to predict. Additionally, round window membrane delivery may result in uneven distribution of drug across the inner ear, as well as poor bioavailability of drugs within the cochlea. In order to compensate for the uneven distribution and the low level of drugs within the cochlea, large volumes of drugs are delivered in the middle ear, producing potential local toxicity. The above-described methods of using the system 900 for trans-round window membrane drug delivery can enable the use of many types of compounds, such as large molecule and lipophobic compounds. The above-described methods provide direct access to the perilymphatic fluid of the cochlea, which can enable more even distribution of the compounds within the inner ear. As the compounds are distributed evenly and directly to the inner ear, smaller volumes of said drugs may be required, which presents a clear treatment improvement over other wasteful techniques.

Figure 14:
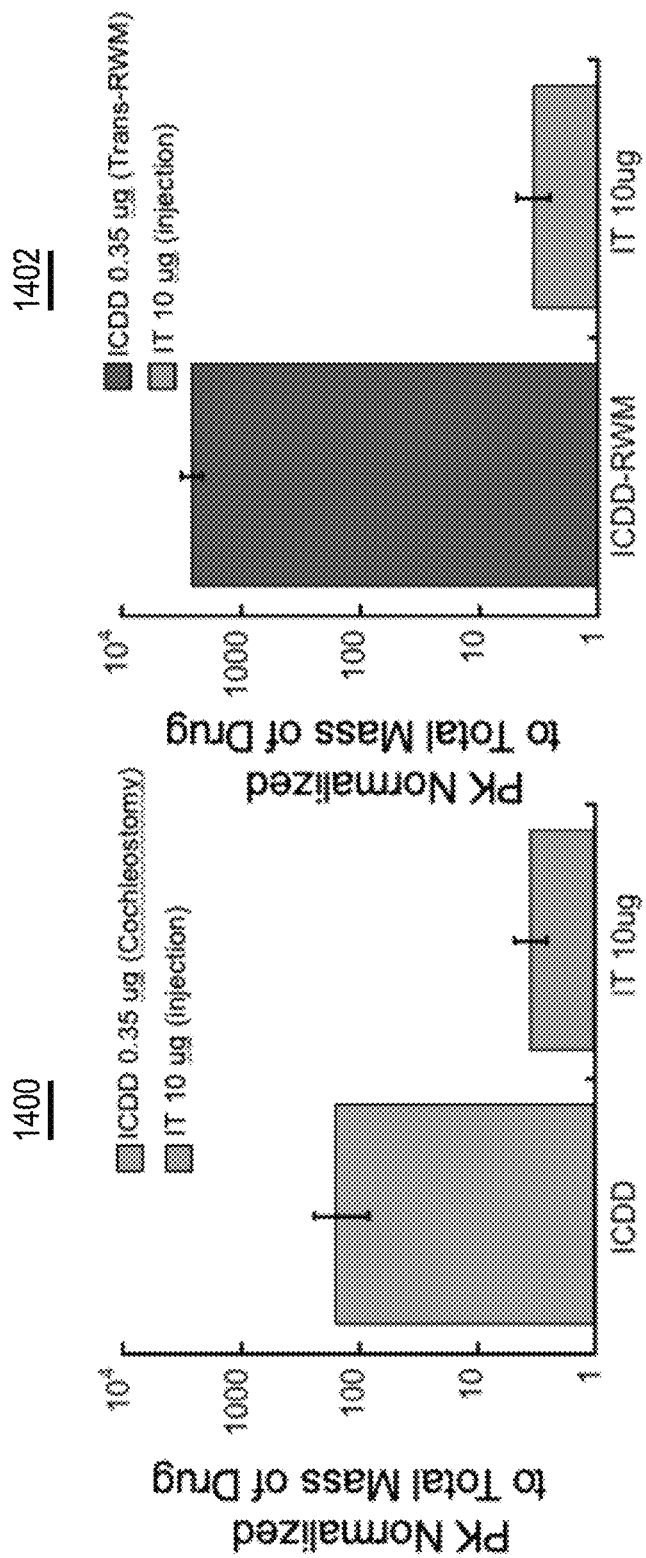
FIGS. 14 and 15 illustrate plots of pharmacokinetics (PK) and pharmacodynamics (PD) across different delivery methods, in accordance with one or more implementations.
Figure 15:
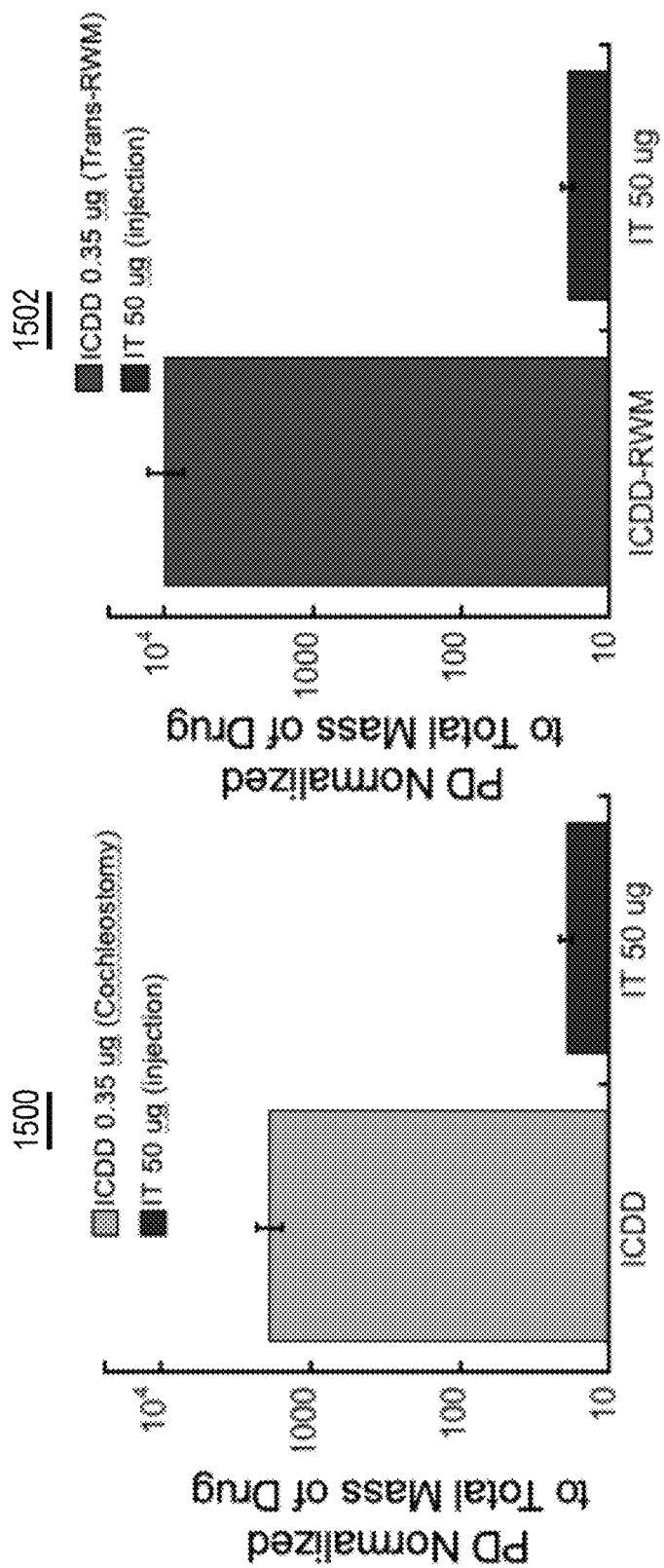

FIGS. 14 and 15 illustrate plots of PK (FIG. 14) and PD (FIG. 15) across different delivery methods. A drug was administered to the inner ear of guinea pigs. The guinea pigs were divided into three different groups. A drug was administered to the guinea pigs of the different groups via a different administration method. A first administration method included intratympanic injection (IT) of the drug. A second administration method included insertion of the cannula into the inner ear via a cochleostomy. A third administration method included insertion of the cannula into the inner ear via the round window membrane. The trans-round window membrane method of the third administration method is similar to the method described above in relation to FIG. 13.

For the cochleostomy and trans-round window membrane experiments, 0.35 μg of the drug was flowed into the inner ear. For the IT experiments, 50 μg of the drug was injected into the inner ear. Referring to FIG. 14, the plot 1400 illustrates the PK, normalized to the total mass of the injected drug, for the cochleostomy injected drug versus the IT injected drug. The plot 1402 illustrates the PK, normalized to the total mass of the injected drug, for the trans-round window membrane injected drug versus the IT injected drug. As illustrated in the plot 1400 and the plot 1402, the PK was the highest in the experiments where the drug was injected with a micropump in a method similar to that described above in relation to FIG. 13. Referring to FIG. 15, the plot 1500 illustrates the PD, normalized to the total mass of the injected drug, for the cochleostomy injected drug versus the IT injected drug. The plot 1502 illustrates the PD, normalized to the total mass of the injected drug, for the trans-round window membrane injected drug versus the IT injected drug. As illustrated in the plot 1500 and the plot 1502, the PD was the highest in the experiments where the drug was injected with a micropump in a method similar to that described above in relation to FIG. 13.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements, and features discussed in connection with one implementation are not intended to be excluded from a similar role in other implementations.

The phraseology and terminology used herein is for the purpose of description and should not be regarded as limiting. The use of "including," "comprising," "having," "containing," "involving," "characterized by," "characterized in that," and variations thereof herein is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the terms "about" and "substantially" will be understood by persons of ordinary skill in the art and will vary to some extent depending upon the context in which they are used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act, or element may include implementations where the act or element is based at least in part on any information, act, or element.

Any implementation disclosed herein may be combined with any other implementation or embodiment, and references to "an implementation," "some implementations," "one implementation," or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description, or any claim are followed by reference signs, the reference signs have been included to increase the intelligibility of the drawings, detailed description, and claims. Accordingly, neither the reference signs nor their absence has any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. A system, comprising:
    a cannula comprising a first end coupled with a micropump and a second end comprising a cannula tip and a stopper positioned at a first predetermined distance from the cannula tip, the stopper configured to enable the cannula tip to be inserted through an anatomic membrane and into a cochlea of a patient, the cannula tip comprising a coating configured to create a seal with the anatomic membrane responsive to insertion of the cannula tip through the anatomic membrane; and
    a handpiece configured to introduce the cannula to the patient, the handpiece comprising:
        a channel defined by a tool shaft of the handpiece, the channel configured to receive the cannula;
        a tip portion coupled with the tool shaft and comprising an outlet in communication with the channel, the tip portion configured to pierce the anatomic membrane of the patient; and
        a collar coupled with the tip portion at a second predetermined distance from the outlet, the collar configured to seat with an anatomic structure of the patient and control a distance that the tip portion can project into the cochlea of the patient,
    wherein the handpiece is configured to be withdrawn from an ear of the patient responsive to seating the cannula into the anatomic structure of the patient, and
    wherein the micropump comprises one or more first layers defining one or more fluid channels, a fluid storage capacitor, and a reservoir, and one or more second layers comprising a pump, the one or more first layers separated from the one or more second layers by a membrane, the membrane forming a ceiling of the fluid storage capacitor, the micropump configured to:
        pump a first fluid from the reservoir into the cochlea of the patient using the pump and the fluid storage capacitor, the first fluid pumped via a micropump outlet coupled to the one or more fluid channels and the cannula, and
        subsequently withdraw a volume of a second fluid from the cochlea of the patient via the micropump outlet and the cannula.

2. The system of claim 1, wherein the micropump is configured for implantation in the patient, and the reservoir is a drug reservoir storing the first fluid.

3. The system of claim 2, wherein the micropump is further configured to pump the first fluid from the drug reservoir to the cochlea of the patient via the cannula.

4. The system of claim 3, wherein the one or more first layers of the micropump further comprise a loading chamber and the one or more second layers of the micropump further comprise a first actuator of a first valve and a second actuator of a second valve, and wherein the micropump is configured to:
    draw the first fluid from the drug reservoir into the loading chamber by opening the first valve via the first actuator and activating the pump; and
    force the first fluid through the micropump outlet to the cannula by closing the first valve via the first actuator, opening the second valve via the second actuator, and activating the pump.

5. The system of claim 1, wherein the handpiece further comprises an angled portion coupling the tip portion to the tool shaft, the angled portion having a second channel in communication with the channel and the outlet of the tip portion.

6. The system of claim 5, wherein at least one of the angled portion or the tip portion are separable from the tool shaft, and the angled portion and the tip portion are configured to couple together using one or more of a snap-on connector, a friction fit connection, a press-fit connection, a knurled nut, or a Luer lock connection.

7. The system of claim 5, wherein the angled portion, the tip portion, and the tool shaft are manufactured from a single contiguous piece of material comprising at least one of stainless steel or a plastic.

8. The system of claim 5, wherein at least one of the angled portion or the tip portion can rotate, while coupled to the tool shaft, around an axis parallel to a length of the tool shaft.

9. The system of claim 1, wherein the tip portion of the handpiece further comprises a needle tip portion, and wherein the needle tip portion is configured to pierce the anatomic membrane of the patient.

10. The system of claim 1, wherein the outlet of the tip portion is positioned at a distal end of the tip portion, the distal end of the tip portion forming an angle between the outlet of the tip portion and a proximal end of the tip portion, wherein the angle is between 70 degrees and 170 degrees, between 75 degrees and 130 degrees, between 90 degrees and 120 degrees, or between 110 degrees and 120 degrees.

11. The system of claim 1, wherein a length of the tool shaft is between about 130 mm and about 170 mm, between about 140 mm and about 160 mm, or between about 140 mm and about 150 mm.

* * * * *